United States Patent
Bovy et al.

(10) Patent No.: US 6,608,246 B1
(45) Date of Patent: Aug. 19, 2003

(54) METHODS FOR MODULATING FLAVONOID CONTENT IN TOMATO BY TRANSFORMATION WITH A CHALCONE ISOMERASE DNA

(75) Inventors: Arnaud Guillaume Bovy, De Bilt (NL); Stephen Glyn Hughes, Essex (GB); Shelagh Rachael Muir, Bedford (GB); Adrianus Joannes Van Tunen, Wageningen (NL); Martine Elisa Verhoeyen, Bedford (GB); Cornelis Henricus De Vos, Wageningen (NL)

(73) Assignee: Lipton, division of Conopco, Inc., Englewood Cliffs, NJ (US)

( * ) Notice: Subject to any disclaimer, the term of this patent is extended or adjusted under 35 U.S.C. 154(b) by 0 days.

(21) Appl. No.: 09/353,242

(22) Filed: Jul. 14, 1999

(30) Foreign Application Priority Data

Jul. 14, 1998 (EP) .......................................... 98305570

(51) Int. Cl.$^7$ .......................... A01H 5/00; A01H 5/08; A01H 5/10
(52) U.S. Cl. ..................... 800/317.4; 800/278; 800/287
(58) Field of Search ............................ 435/69.1, 320.1, 435/419, 468; 800/278, 298

(56) References Cited

FOREIGN PATENT DOCUMENTS

| EP | 0 335 451 | 10/1989 |
|----|-----------|---------|
| WO | WO 90/11682 | 10/1990 |
| WO | WO 94/03606 | 2/1994 |
| WO | WO 99/14351 | 3/1999 |
| WO | 99/37794 | 7/1999 |

OTHER PUBLICATIONS

Koziel, M. G. et al., "Optimizing expression of transgenes with an emphasis on post–transcriptional events." 1996, Plant Molecular Biology, vol. 32, pp. 393–405.*
Stam, M. et al., "The Silence of Genes in Transgenic Plants." 1997, Annals of Botany, vol. 79, pp. 3–12.*
De Luca, V., "Molecular characterization of secondary metabolic pathways." 1993, AgBiotech News and Information, vol. 5, pp. 225N–229N.*
Sparvoli et al. Cloning and molecular analysis of structural genes involved in flavonoid and stilbene biosynthesis in grape (*Vitis vinifera* L.) Plant Biol. 24 743–755 (1994).*
Bylden et al. "Sequence analysis of a chalcone isomerase cDNA of *Phaseolus vulgaris* L." Plant Mol. Biol. 16: 167–169 (1991).*
Shirley et al. "Effects of ionizing radiation on a plant genome: Analysis of two Arabidopsis transparent testa mutations." Plant Cell 4: 333–347 (1992).*
Mehdy et al. "Chalcone isomerase cDNA cloning and mRNA induction by fungal elicitor, wounding and infection." EMBO J. 6: 1527–1533 (1987).*
Wood et al. "A cDNA encoding chalcone isomerase from aged pea epicotyls." Plant Gene Register 104: 1463–1466 (1994).*
Phytochemistry, (1980), vol. 19, pp. 1415–1419, *Phenolic Constituents of Tomato Fruit Cuticles*.
The Lancet, (1993), vol. 342, pp. 1007–1011, *Dietary Antioxidant Flavonoids and Risk of Coronary Heart Disease: the Zutphen Elderly Study*.
Nutritional Biochemistry, (1996), vol. 7, pp. 66–76, *Flavonoids—Chemistry, metabolism, cardioprotective effects, and dietary sources*.
Free Radical Research, (1995), vol. 22, No. 4, pp. 375–383, *the Relative Antioxidant Activities of Plant–Derived Polyphenolic Flavonoids*.
Trends in Plant Science, (1997), vol. 2, pp. 152–159, *Anitoxidant properties of phenolic compounds*.
BioEssays, (1994), vol. 16, No. 2 (1994), *The Flavonoid Biosynthetic Pathway in Plants: Function and Evolution*, pp. 123–132.
The Plant Cell, vol. 2, p. 279 (Abstract), (1990), *Introduction of a Chimeric Chalcone Synthase Gene into Petunia Results in Reversible Co–Suppression of Homologous Genes in trans*.
The Plant Cell, vol. 9, pp. 1357–1368, (1997), *The Frequency and Degree of Cosuppression by Sense Chalcone Synthase Transgenes Are Dependent on Transgene Promoter Strength and Are Reduced by Premature Nonsense Condons in the Transgene Coding Sequence*.
Plant Physiol, (1996), vol. 112, pp. 1617–1624, *Overexpression of ₁–Phenylalanine Ammonia–Lyase in Transgenic Tobacco Plants Reveals Control Points for Flux into Phenylpropanoid Biosyntheses*.
Plant Cell Physiol, 36(6), pp. 1023–1031 (1995), *Molecular Cloning and Characterization of Rosa hybrida Dihydroflavonol 4– reductase Gene*.
Plant Molecular Biology, vol. 12, No. 5, (1989), pp. 539–551, *Regulation of Chalcone Flavone Isomerase (Chi) Gene Expression in Petunia Hydrida: The Use of Alternative Promoters in Corolla, Anthers and Pollen*.
Molecular and General Genetics, vol. 242, (1994), pp. 1–8, *Isolation and Characterization of a Maize Gene Encoding Chalcone Flavonone Isomerase*.
EMBL Sequence Database, (1992), *Structure of an Elicitor–Inducible Chalcone Isomerase Gene in Phaseolus Vulgaris* Accession No. 215046.
The EMBO Journal, vol. 7, No. 5, pp. 1257–1263 (1988), *Cloning of the two chalcone flavanone isomerase genes from Petunia Hybride: coordinate, light–regulated and differential expression of flavonoid genes*.

* cited by examiner

*Primary Examiner*—Amy J. Nelson
(74) *Attorney, Agent, or Firm*—Gerard J. McGowan, Jr.

(57) ABSTRACT

A method for manipulating the production of flavonoids in tomatoes by expressing genes encoding chalcone isomerase, compositions for use in such a method and tomato plants having altered flavonoid levels are disclosed.

13 Claims, 12 Drawing Sheets

Fig.2.
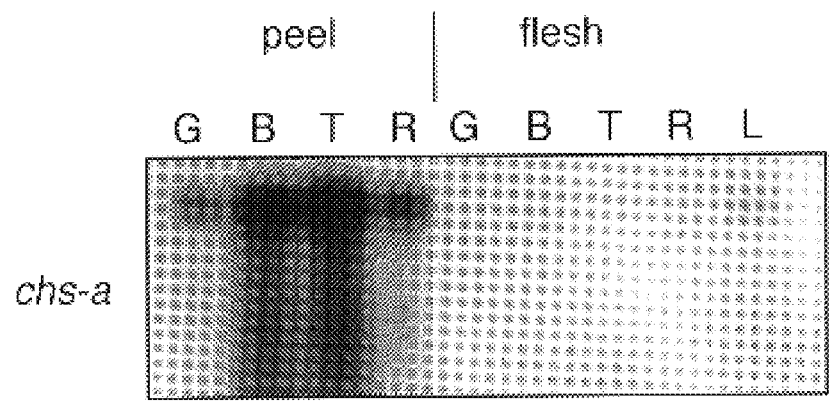
chs-a
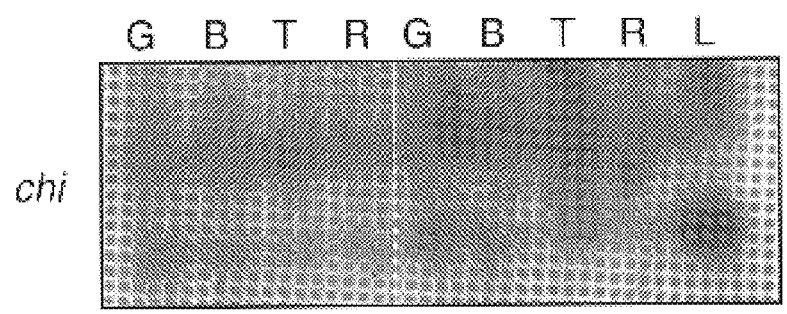
chi
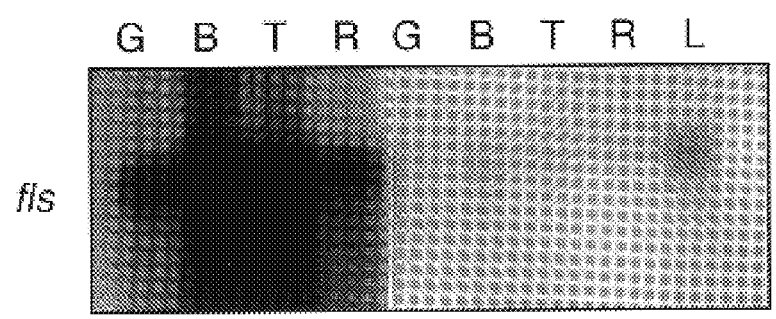
fls

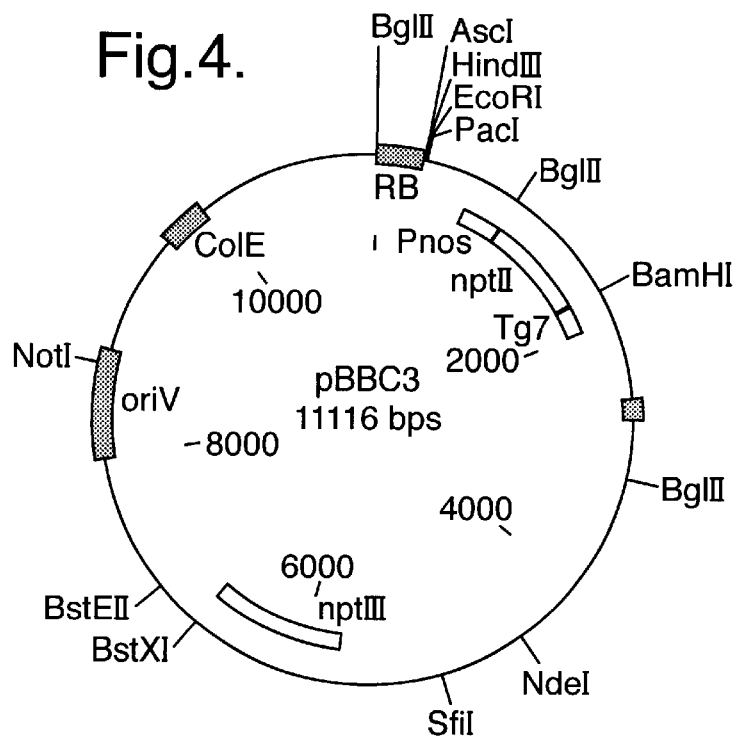
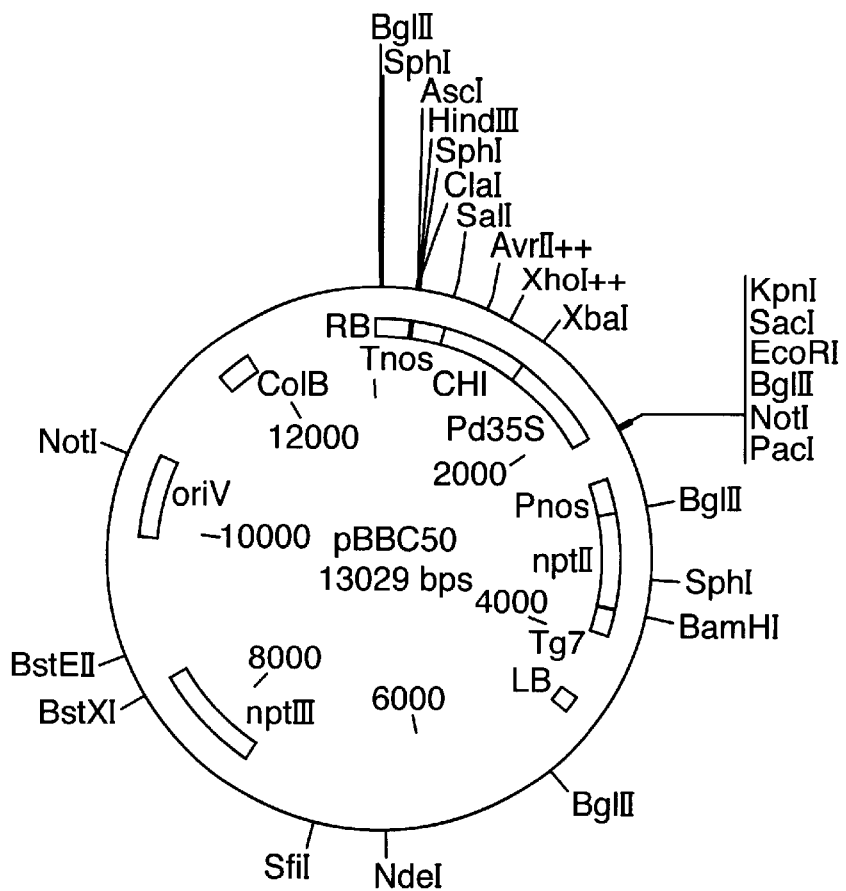
Fig. 4.

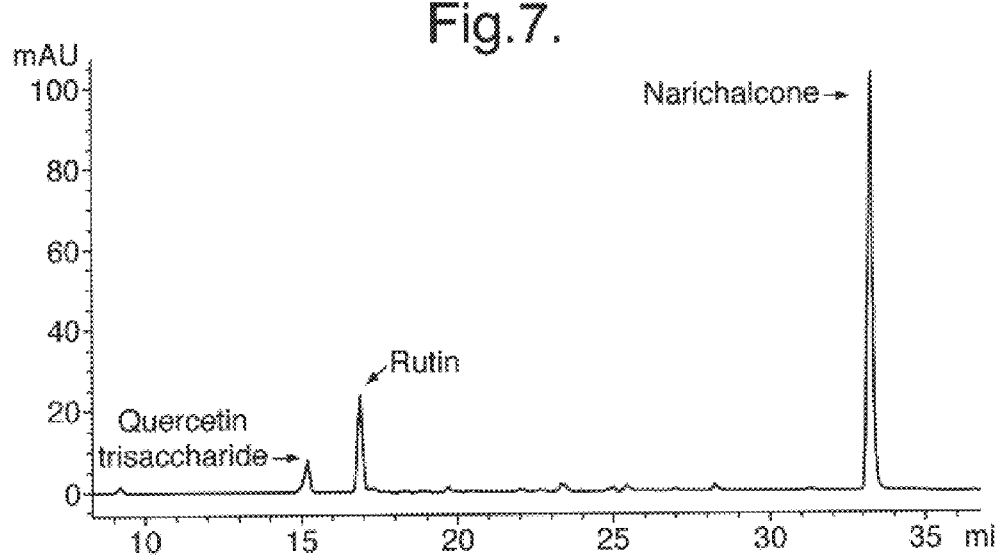
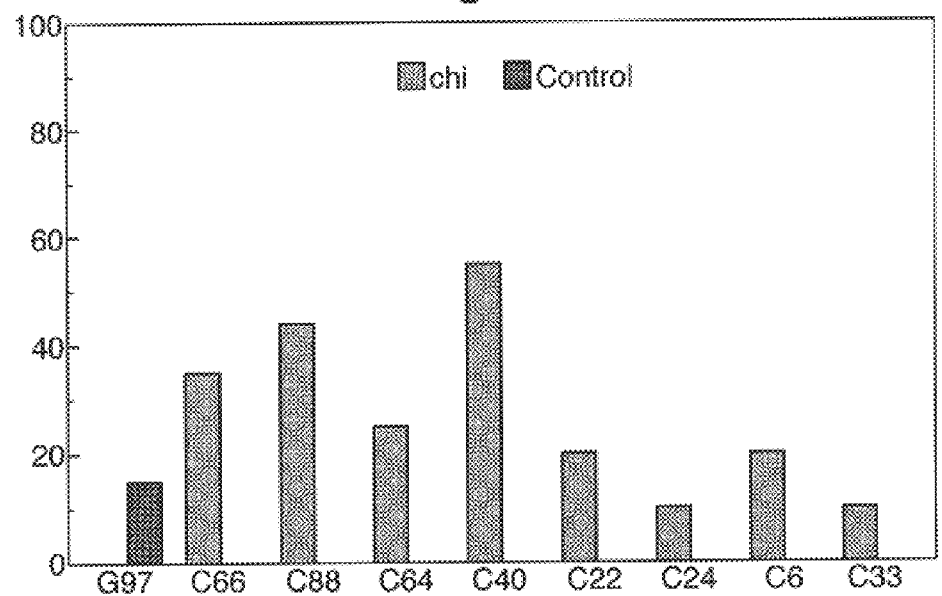

Fig. 12.
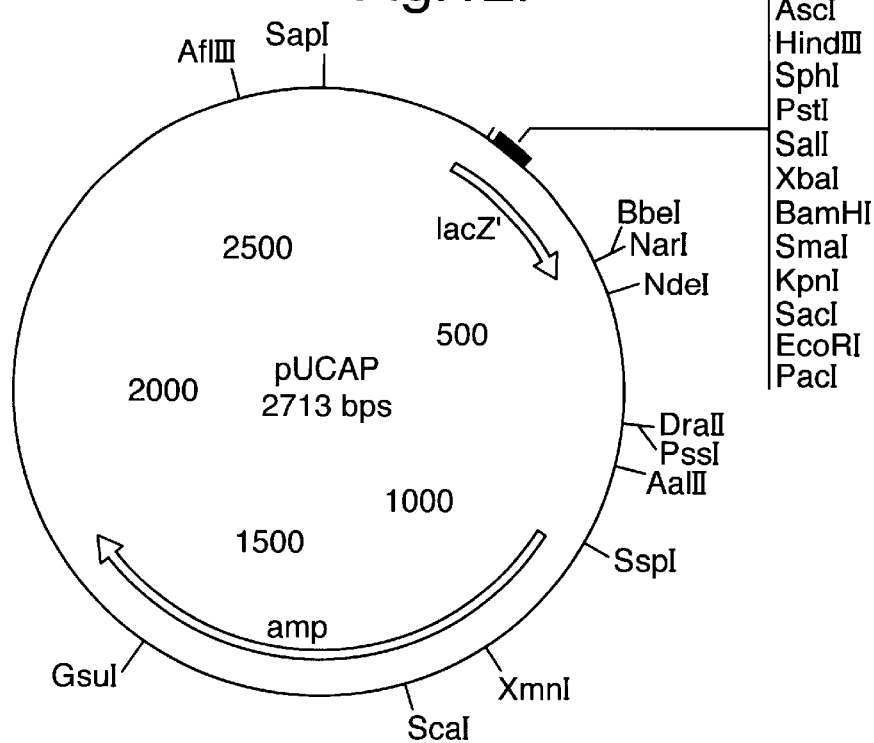
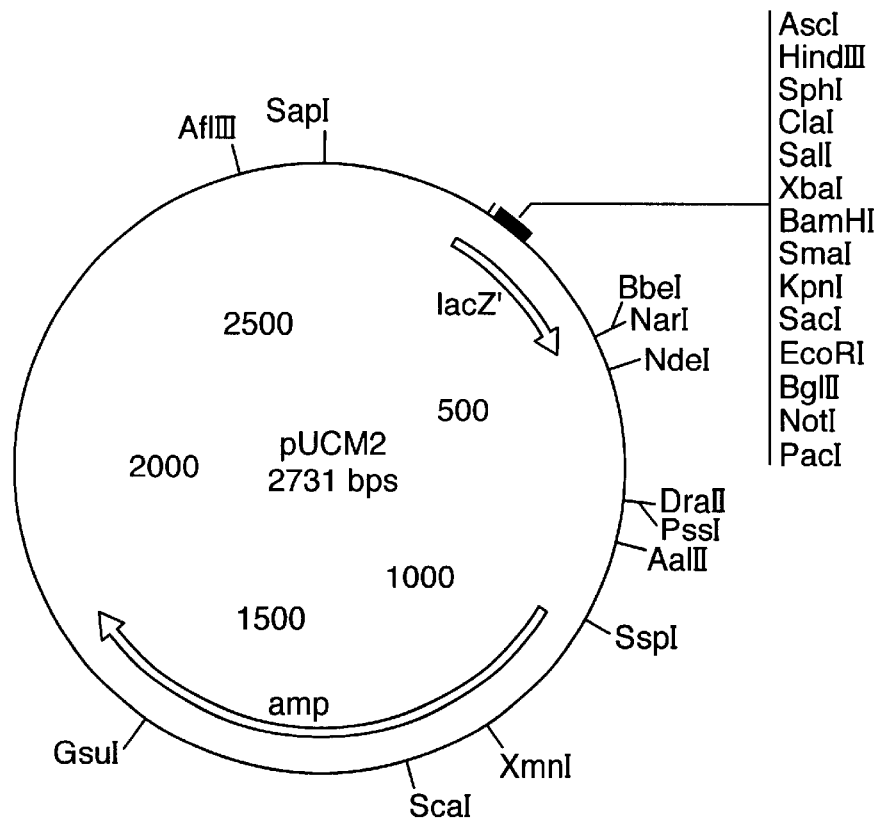

```
GGCGCGCCAAGCTTGCATGCATCGATATGGTCGACTCTAGAGGATCCCCGGGTACCGAG
CTCGAATTCCAGATCTGCGGCCGCTTAATTAA
```

METHODS FOR MODULATING FLAVONOID CONTENT IN TOMATO BY TRANSFORMATION WITH A CHALCONE ISOMERASE DNA

FIELD OF THE INVENTION

The present invention relates generally to methods for manipulating the production of flavonoids in plants by manipulating endogeneous and incorporated gene activity in the flavonoid biosynthetic pathway and compositions for use in such methods. In particular, it relates to methods for increasing flavonoid levels by altering the level of chalcone isomerase activity. Chalcone isomerase is an enzyme involved in the biosynthetic pathway of flavonoids.

BACKGROUND OF THE INVENTION

Flavonoids form a large group of polyphenolic compounds, based on a common diphenylpropane skeleton, which occur naturally in plants. Included within this class of compounds are flavonols, flavones, flavanones, catechins, anthocyanins, isoflavonoids, dihydroflavonols and stilbenes. The flavonoids are mostly present as glycosides.

In tomato fruits, the main flavonoid found is naringenin chalcone (Hunt et al, Phytochemistry, 19, (1980), 1415–1419). It is known to accumulate almost exclusively in the peel and is simultaneously formed with colouring of the fruit. In addition to naringenin chalcone, glycosides of quercetin and, to a lesser extent, kaempferol are also found in tomato peel.

Reports in the literature suggest that there is increasing evidence that flavonoids are potentially health-protecting components in the human diet. Epidemiological studies suggest a direct relationship between cardioprotection and increased consumption of flavonoids, in particular flavonols of the quercetin and kaempferol type, from dietary sources such as onion, apples and tea (see, for example, Hertog et al, Lancet, 342 (1993), 1007–1011).

Flavonoids have been reported to exhibit a wide range of biological activities in vitro including anti-inflammatory, anti-allergic and vasodilatory activity (Cook et al, Nutritional Biochemistry, 7, (1996), 66–76). Such activity has been attributed in part to their ability to act as antioxidants, capable of scavenging free radicals and preventing free radical production. Within this group of compounds, those having the most potent antioxidant activity are the flavonols (Rice-Evans et al, Free Radical Research, 22, (1995), 375–383). In addition, flavonoids can also inhibit the activity of key processes such as lipid peroxidation, platelet aggregation and capillary permeability (see Rice-Evans et al, Trends in Plant Science, 2, (1997), 152–159).

Based on studies of this type, there is presently considerable interest in the development of food products from plants rich in such protective flavonoids.

It would be desirable to produce plants which intrinsically possess elevated levels of health protecting compounds such as flavonoids in order to develop food products with enhanced protective properties. Traditionally, the approach to improving plant varieties has been based on conventional cross-breeding techniques, but these are slow as they require time for breeding and growing successive plant generations. More recently, recombinant DNA technology has been applied to the general problem of modifying plant genomes to produce plants with desired phenotypic traits. Whilst reference has been made in the literature to the use of genetic manipulation techniques in modifying the flavonoid biosynthetic pathway, as discussed beneath, it is notable that these attempts have been directed in general towards modifying pigmentary anthocyanin production.

The flavonoid biosynthetic pathway is well established and has been widely studied in a number of different plant species (see, for example, Koes et al, BioEssays, 16, (1994), 123–132). Briefly, three molecules of malonyl-CoA are condensed with one molecule of Coumaroyl-CoA, catalysed by the enzyme chalcone synthase, to give naringenin chalcone which rapidly isomerises, catalysed by chalcone isomerase, to naringenin. Subsequent hydroxylation of naringenin catalysed by flavanone 3-hydroxylase leads to dihydrokaempferol. Dihydrokaempferol itself can be hydroxylated to produce either dihydroquercetin or dihydromyricetin. All three dihydroflavonols subsequently can be converted to anthocyanins (by the action of dihydroflavonol reductase and flavonoid glucosyltransferase) or alternatively converted to flavonols such as kaempferol, quercetin and myricetin by the action of flavonol synthase.

A schematic overview of the flavonoid biosynthetic pathway is presented in appendix 1, FIG. 1.1.

The manipulation of flavonoid levels in plants by altering the expression of a single flavonoid biosynthetic gene is disclosed by Napoli (1990, Plant Cell, 2:279–289). Napoli discloses the introduction of a chimeric chalcone synthase (CHS) gene into Petunia. Said introduction is described to result in a block in the anthocyanin biosynthesis. The resulting transformed petunia plants therefore contained lower levels of flavonoids than untransformed plants, presumably due to co-suppression of the endogeneous CHS activity.

Que (1997, Plant Cell, 9: 1357–1368) discloses a comparison of the effect of strong and weak promoters that drive sense chalcone synthase transgenes in large populations of independently transformed plants. It is shown that a strong transgene promoter is required for high frequency cosuppression of CHS genes and for the production of a full range of phenotypes.

Howles (1996, Plant Physiol. 112: 1617–1624) discloses the stable genetic transfer of the flavonoid biosynthetic gene phenylalanine ammonia-lyase (PAL) from french bean into tobacco. A proportion of the obtained transgenic tobacco plants is shown to display overexpression of PAL activity. According to Howles PAL overexpressing plants do not contain altered levels of flavonoids.

It has been disclosed by Tanaka et al (1995, Plant and Cell Physiology 36: 6, 1023–1031) that heterologous transformation of dihydroflavonol reductase (DFR) can be used for the production of plants with altered levels of anthocyanins.

There is no disclosure in the literature of the manipulation of flavonoids in plants by means of overexpression of chalcone isomerase.

Accordingly, there remains a continuing need for the development of methods for enhancing the levels of flavonoids, in particular flavonols, in plants.

SUMMARY OF THE INVENTION

Therefore, in a first aspect, the invention provides a method for producing a plant capable of exhibiting altered levels of flavonoids comprising incorporating into said plant one or more gene sequences encoding a protein with chalcone isomerase activity, or incorporating a nucleotide sequence encoding a protein functionally equivalent thereto.

The invention also provides a plant having one or more transgenes each encoding a protein with chalcone isomerase activity, or a protein functionally equivalent thereto, incorporated into its genome such that its ability to produce flavonoids is altered.

According to a highly preferred embodiment, the invention further provides a tomato plant having one or more transgenes each encoding a protein with chalcone isomerase activity, or a protein functionally equivalent thereto, incorporated into its genome such that its ability to produce flavonoids is altered.

Also provided is a transformed plant having enhanced flavonoid levels, not being chalcones, particularly enhanced flavonol levels compared to similar untransformed plants. Preferably the level of said flavonoids, not being chalcones, in transformed plants is at least 4 times higher than in similar untransformed plants, more preferred 5–100, most preferred 10–40 times higher than in similar untransformed plants.

Further provided is a fruit-bearing plant, particularly a tomato plant, having flavonoids, particularly flavonols, in the peel of the fruit.

Seeds, fruits and progeny of such plants and hybrids are also included within the invention.

The invention further provides DNA constructs coding for a protein with chalcone isomerase activity, or a functionally equivalent sequence of said DNA construct, operably linked to a promoter.

When transformed into a plant cell, these constructs are useful for overexpressing genes encoding proteins with chalcone isomerase activity, thereby altering the ability of the plant to produce flavonoids. The invention also provides for plants comprising these constructs together with seeds, fruits and progeny thereof.

Food products such as sauces, dressings, ketchups and soups, comprising at least part of a plant prepared according to the invention are also provided.

Also provided are skin and hair protective products comprising at least part of a plant according to the invention.

Also provided are pharmaceuticals comprising at least part of a plant according to the invention.

Definition of Terms

As used herein, "plant" means a whole plant or part thereof, or a plant cell or group of plant cells. It will be appreciated that also extracts are comprised in the invention.

A "flavonoid" or a "flavonol" may suitably be an aglycon or a conjugate thereof, such as a glycoside, or a methyl, acyl, sulfate derivative.

A "protein with chalcone isomerase activity" is a protein being capable of enzymatically catalysing the conversion of a chalcone into a flavanone, for example narichalcone into naringenin.

A "gene" is a DNA sequence encoding a protein, including modified or synthetic DNA sequences or naturally occurring sequences encoding a protein, and excluding the 5' sequence which drives the initiation of transcription.

A "DNA sequence functionally equivalent thereto" is any sequence which encodes a protein which has similar functional properties.

According to another embodiment, a functionally equivalent DNA sequence shows at least 50% similarity to the respective DNA sequence. More preferably a functionally equivalent DNA sequence shows at least 60%, more preferred at least 75%, even more preferred at least 80%, even more preferred at least 90%, most preferred 95–100% similarity, to the respective DNA sequence.

According to the most preferred embodiment a functionally equivalent DNA sequence shows not more than 5 base pairs difference to the respective DNA sequence, more preferred less than 3, e.g. only 1 or 2 base pairs different.

According to another embodiment a functionally equivalent sequence is preferably capable of hybridising under low stringent conditions to the respective sequence.

"Breaker" is the ripening stage corresponding to the appearance of the first flush of colour on the green fruit.

"Operably linked to one or more promoters" means the gene, or DNA sequence, is positioned or connected to the promoter in such a way to ensure its functioning. The promoter is any sequence sufficient to allow the DNA to be transcribed. After the gene and promoter sequences are joined, upon activation of the promoter, the gene will be expressed.

A "construct" is a polynucleotide comprising nucleic acid sequences not normally associated in nature.

An "altered" level of flavonoids is used throughout this specification to express that the level of specific flavonoids in the transformed plants differs from the level of flavonoids present in untransformed plants. Preferably the difference is between 0.1 and 100 fold. It will be appreciated that the specific flavonoids as meant here are flavonoids other than chalcones as said specific flavonoids are formed at the expense of chalcones.

Therefore in the specification where these flavonoids are meant reference will be made to "specific flavonoids".

An "increased" level of flavonoids is used to indicate that the level of is preferably at least 4 times higher than in similar untransformed plants, more preferred 5–100, most preferred 10–40 times higher than in similar untransformed plants.

BRIEF DESCRIPTION OF THE DRAWINGS

The present invention may be more fully understood by reference to the following description, when read together with the accompanying drawings in which:

FIG. 2 shows the northern analysis of tomato fruit harvested at different developmental stages, denoted as: green (G), breaker (B), turning (T) and red (R), and separated into peel and flesh. Leaves (L) were harvested from young tomato plants. RNA was isolated from the samples, separated on formaldehyde-agarose gels, blotted and hybridised with petunia chs-a, chi and fls probes.

FIG. 7 shows a typical HPLC chromatogram, recorded at 360 nm, of a non-hydrolysed extract of peel tissue of a tomato plant transformed with the control plasmid pSJ89. Peaks corresponding to rutin, quercetin trisaccharide and narichalcone are indicated.

FIG. 8 shows levels of quercetin in hydrolysed extracts of flesh of tomatoes transformed with either the control pSJ89 (G series of transformed plants) or the pBBC50 (C series of transformed plants) gene constructs.

FIG. 12 shows restriction maps of plasmids pUCAP and pUCM2.

DETAILED DESCRIPTION OF THE INVENTION

Figure 1A:
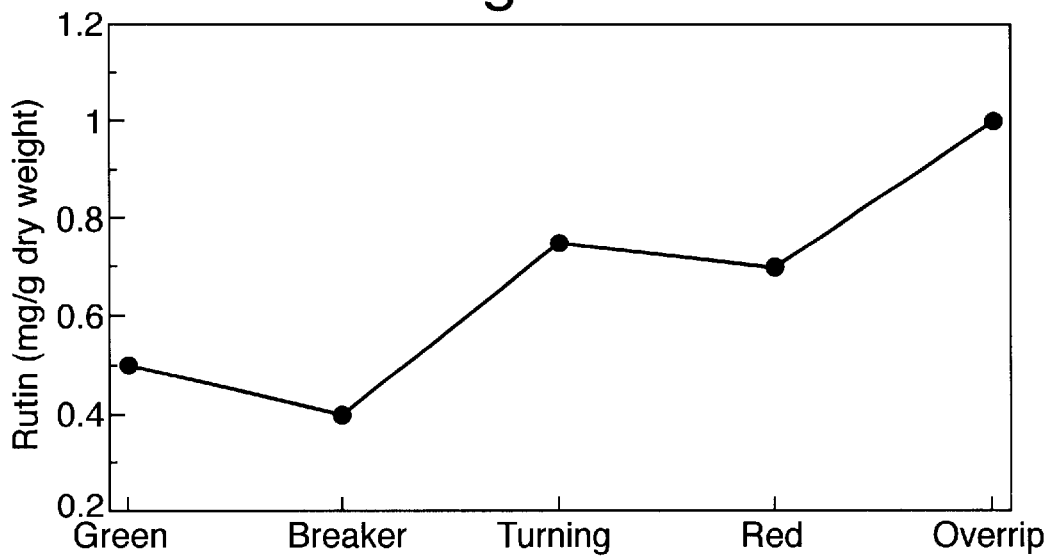
FIGS. 1A–1B shows the levels of the two dominant flavonoids, rutin (A.) and narichalcone (B.) in FM6203 tomato peel during ripening. Results represent the means of three independent samples.

The present invention is based on the unexpected finding that chalcone isomerase may be a rate limiting step in the production of flavonoids in tomato fruit.

We have surprisingly found that upon incorporation of a gene sequence encoding for a protein with chalcone isomerase activity in plants, the subsequent overexpression of this protein leads to very high (sometimes even 50–100 fold) increase in the amount of flavonoids in the fruit of said plant.

Applicants have found that in ripening tomato fruit two dominant flavonoids can be detected: flavonol rutin and narichalcone, which both accumulate in the peel of tomato fruit. At no developmental stage were significant amounts of flavonoids detected in the flesh of fruit. Without wishing to be bound by any theory applicants believe that the accumulation of narichalcone in the peel of fruit before declining through the red and over ripe stages, is indicative that chalcone isomerase represents a rate limiting step in the formation of flavonoids.

A method for elucidation of the rate limiting step in flavonoid biosynthesis is further illustrated in the examples.

Advantageously, by means of the invention, levels of specific flavonoids, more particularly flavonols, in plants, particularly tomatoes, may be altered. Preferably in the method according to the invention the levels of flavonoids, more particularly flavonols, in plants, particularly tomatoes, are increased. Moreover, it has been found that the level of flavonoids, in particular the level of specific flavonols, may be increased specifically in the peel of tomato fruit, thereby producing tomatoes with enhanced nutritional, preservative and flavour characteristics.

Most preferred in the method according to the invention the transformed plant exhibits increased levels of kaempferol and/or quercetin, or their glycosides or derivatives thereof.

It will be appreciated that the invention furthermore relates to a method for producing a plant capable of exhibiting altered levels of flavonoids, comprising incorporating into said plant a gene sequence encoding for chalcone isomerase, thereby increasing the level of flavonoids by overexpression of said chalcone isomerase. Therefore it will be understood that the invention encompasses said gene sequence encoding for chalcone isomerase and any sequence functionally equivalent thereto. This group of sequences is in the course of this application also referred to as "a gene comprising a nucleotide sequence encoding an enzyme with chalcone isomerase activity".

Therefore according to a further embodiment the invention relates to a method for producing a plant capable of exhibiting altered levels of flavonoids comprising incorporating into said plant a gene comprising a nucleotide sequence encoding an enzyme with chalcone isomerase activity.

According to a preferred embodiment said gene comprises a nucleotide selected from:
(i) a nucleotide sequence, encoding an amino acid sequence having at least 40% similarity, to seq ID No1;
(ii) a nucleotide sequence capable of hybridising under low stringent conditions to a sequence selected from the group of sequences set forth under (i) above;
(iii) a nucleotide sequence encoding a protein that is functionally equivalent to the protein encoded by seq ID no 1.

Seq, ID 1 is an amino acid sequence obtainable from PIR database, accession number SO4725, as published by van Tunen et al, EMBO J. 7, 1257–63 1988.

More preferred said gene comprises the nucleotide sequence encoding an amino acid sequence having at least 60% similarity preferably at least 90%, more preferred at least 95% or even 98%, similarity to the sequence as set forth in seq ID No1 (amino acid sequence of chalcone isomerase).

According to a highly desired embodiment, the gene which is incorporated into the plant in the method according to the invention encodes the amino acid sequence of chalcone isomerase from petunia as set forth in seq ID No 1.

According to a preferred embodiment said nucleotide sequence comprises a sequence which has at least 50% similarity, more preferred at least 60%, even more preferred at least 75%, even more preferred at least 80%, still more preferred at least90%, most preferred at least 95% or even 98–100% similarity to Sequence ID no 2, and whereby said sequence encodes a protein having chalcone isomerase activity.

Although the percentage similarity referred to above assumes an overall comparison between the sequence set forth in at least one of the sequences of Seq ID 1, Seq ID 2, it is clear that there may be specific regions within molecules being compared, having less than 60% similarity.

It will be appreciated that the invention extends to any plant which is amenable to transformation.

Therefore, according to another embodiment, the invention repates to a plant having one or more transgenes, each encoding a protein with chalcone isomerase activity or a protein functionally equivalent thereto, incorporated into its genome such that its ability to produce flavonoids is altered.

Preferably the plants according to the invention are suitable for human consumption. Suitable plants are for example vegetables, fruits, nuts, herbs, spices, infusion materials. Suitable vegetables are for example from the Pisum family such as peas, family of Brassicae, such as green cabbage, Brussel sprouts, cauliflower, the family of Phaseolus such as barlotti beans, green beans, kidney beans, the family of Spinacea such as spinach, the family of Solanaceae such as potato and tomato, the family of Daucus, such as carrots, family of Capsicum such as green and red pepper, and berries for example from the family of Ribesiaceae, Pomaceae, Rosaceae, for example strawberries, black berries, raspberries, black current and edible grasses from the family of Gramineae such as maize, and citrus fruit for example from the family of Rutaceae such as lemon, orange, tangerine. Also preferred are plants which can form the basis of an infusion such as black tea leaves, green tea leaves, jasmin tea leaves. Also preferred is the tobacco plant.

A particularly preferred plant for use in the method according to the invention is the tomato plant.

It will furthermore be appreciated that the sequence encoding a protein with chalcone isomerase activity may be a genomic or cDNA clone, or a sequence which in proper reading frame encodes an amino acid sequence which is functionally equivalent to the amino acid sequence of the protein encoded by the genomic or cDNA clone. By "functionally equivalent" is meant any DNA sequence which is capable of similar biological activity. A functional derivative can be characterised by an insertion, deletion or a substitution of one or more bases of the DNA sequence, prepared by known mutagenic techniques such as site-directed mutagenesis. The functionality can be evaluated by routine screening assays, for example, by assaying the flavonoid content of the resulting transgenic plant. An in, vitro assay to determine chalcone isomerase activity has been described by van Weely (1983, *Planta* 159: 226–230).

Gene sequences encoding a gene sequence for proteins with chalcone isomerase activity for use according to the present invention may suitably be obtained from plants, in particular higher plants as these generally possess a flavonoid biosynthetic pathway. Suitable gene sequences can for example be obtained from petunia, maize, arabidopsis, alfalfa, pea, bean, grape, apple.

The gene sequences of interest are preferably operably linked (that is, positioned to ensure the functioning of) to one or more suitable promoters which allow the DNA to be transcribed. Said promoters are preferably promoters useful to obtain over-expression of the protein with chalcone isomerase activity in said host plant. Suitable promoters, which may be homologous or heterologous to the gene (that is, not naturally operably linked to the expressed gene encoding a chalcone isomerase protein or a functional equivalent thereof) useful for expression in plants are well known in art, as described, for example, in Weising et al, (1988), Ann. Rev. Genetics, 22, 421–477). Promoters for use according to the invention may be inducible, constitutive or tissue-specific or have various combinations of such characteristics. Useful promoters include, but are not limited to, constitutive promoters such as carnation etched ring virus (CERV), cauliflower mosaic virus (CaMV) 35S promoter, or more particularly the enhanced cauliflower mosaic virus promoter, comprising two CaMV 35S promoters in tandem (referred to as "Double 35S"), or the GBSS (granular bound starch synthase) promoter.

According to a preferred embodiment fruit specific promoters are used. Suitable fruit-specific promoters include the tomato E8 promoter (Deikman et al, (1988), EMBO J, 7, 3315–3320), 2A11 (Van Haaren et al, Plant Mol Biol, 21, 625–640), E4 (Cordes et al, (1989), Plant Cell, 1, 1025–1034) and PG (Bird et al, (1988), Plant Mol. Biol., 11, 651–662,) Nicholass et al, (1995), Plant Molecular Biology, 28, 423–435, pTOM96 (ref), fpbll(WO-A-91/05054).

In another preferred embodiment, the promoter is a constitutive enhanced 35S CaMV promoter.

It will be appreciated that accumulation of flavonoids may be inhibited by the rate of production of the amino acid phenylalanine, the primary substrate in the synthesis of phenylpropanoids and subsequent flavonoids. In order to increase phenylalanine biosynthesis, genes encoding enzymes of the phenylalanine pathway that are insensitive to feed-back regulation may be introduced as an optional additional step.

Preferably the desired gene sequences, operably linked to respective suitable promoters, are fused to appropriate expression sequences to provide an expression cassette functional in a plant cell which can be introduced into a plant cell by any conventional plant transformation method.

Therefore the invention also relates to a DNA construct comprising sequences encoding for a protein with chalcone isomerase activity, or a functionally equivalent sequence thereof, operably linked to a promoter; and relates to plants, preferably tomato plants comprising said DNA construct.

Accordingly, the invention provides in a further aspect an expression cassette comprising as operably linked components in the 5'–3' direction of transcription at least one unit, comprising a promoter functional in a plant cell, a gene sequence encoding a protein with chalcone isomerase activity and a transcriptional termination regulatory region functional in a plant cell.

The promoter and termination regulatory regions will be functional in the host plant cell and may be heterologous (that is, not naturally occurring) or homologous (derived from the plant host species) to the plant cell and the gene. Suitable promoters which may be used are described above.

The termination regulatory region may be derived from the 3' region of the gene from which the promoter was obtained or from another gene. Suitable termination regions which may be used are well known in the art and include *Agrobacterium tumefaciens nopaline* synthase terminator (Tnos), *Agrobacterium tumefaciens mannopine* synthase terminator (Tmas) and the CaMV 35S terminator (T35S). Particularly preferred termination regions for use according to the invention include the tobacco ribulose bisphosphate carboxylase small subunit termination region (TrbcS) or the Tnos termination region.

Such gene constructs may suitably be screened for activity by transformation into a host plant via Agrobacterium and screening for flavonoid levels.

Conveniently, the expression cassette according to the invention may be prepared by cloning the individual promoter/gene/terminator unit into a suitable cloning vector. Suitable cloning vectors are well known in the art, including such vectors as pUC (Norrander et al, (1983, Gene 26, 101–106), pEMBL (Dente et al (1983), Nucleic Acids Research, 11, 1645–1699), pBLUESCRIPT (available from Stratagene), pGEM (available from Promega) and pBR322 (Bolivar et al, (1977), Gene, 2, 95–113). Particularly useful cloning vectors are those based on the pUC series. The cloning vector allows the DNA to be amplified or manipulated, for example, by adding sequences. The cloning sites are preferably in the form of a polylinker, that is a sequence containing multiple adjacent restriction sites, so as to allow flexibility in cloning.

In a particularly preferred embodiment, the individual promoter/gene/terminator units are cloned into adjacent pairs of restriction sites in a suitable cloning vector.

Suitably, the nucleotide sequences for the genes may be extracted from any nucleotide database and searched for restriction enzymes that do not cut. These restriction sites may be added to the genes by conventional methods such as incorporating these sites in PCR primers or by sub-cloning.

Preferably the DNA construct according to the invention is comprised within a vector, most suitably an expression vector adapted for expression in an appropriate host (plant) cell. It will be appreciated that any vector which is capable of producing a plant comprising the introduced DNA sequence will be sufficient.

Suitable vectors are well known to those skilled in the art and are described in general technical references such as Pouwels et al, Cloning Vectors. A laboratory manual, Elsevier, Amsterdam (1986). Particularly suitable vectors include the Ti plasmid vectors.

Transformation techniques for introducing the DNA constructs according to the invention into host cells are well known in the art and include such methods as microinjection, using polyethylene glycol, electroporation, or high velocity ballistic penetration. A preferred method for use according to the present invention relies on agrobacterium—mediated transformation.

After transformation of the plant cells or plant, those plant cells or plants into which the desired DNA has been incorporated may be selected by such methods as antibiotic resistance, herbicide resistance, tolerance to amino-acid analogues or using phenotypic markers.

Various assays may be used to determine whether the plant cell shows an increase in gene expression, for example, Northern blotting or quantitative reverse transcriptase PCR (RT-PCR). Whole transgenic plants may be regenerated from the transformed cell by conventional methods. Such transgenic plants having improved flavonoid levels may be propagated and crossed to produce homozygous lines. Such plants produce seeds containing the genes for the introduced trait and can be grown to produce plants that will produce the selected phenotype.

In accordance with a particular embodiment of the invention, the cloning vectors plasmid pUCM2 and pUCM3 were prepared by modifying the cloning vector pUCAP (Van Engelen et al, (1995), Transgenic Research, 4, 288–290).

The invention furthermore relates to a plant having one or more transgenes each encoding a protein with chalcone isomerase activity, or a sequence functionally equivalent thereto, incorporated into its genome such that its ability to produce flavonoids is altered.

The invention also encompasses a tomato plant prepared according to the method of the invention.

The following examples are provided by way of illustration only.

DNA manipulations were performed using standard procedures well known in the art, as described, for example, in Sambrook et al, Molecular Cloning, A Laboratory Manual, Second Edition, Cold Spring Harbour Laboratory Press, 1989 (hereinafter "Sambrook").

The following literature references are mentioned in the Examples:
Becker, D. et al. (1992) Plant Mol. Biol. 20: 1195–1197
Bovy, A. G. et al. (1995) Acta Hortic. 405: 179–189.
Fulton, T. M. et al. (1995) Plant Mol. Biol. Rep. 13: 225–227
Hanahan, D. (1983) J. Mol. Biol. 166: 557–580.
Hertog, M. G. L. et al. (1992) J. Agric. Food Chem. 40: 1591–1598.
Hoekema, A. et al. (1985) Plant Mol. Biol. 5: 85–89
Jefferson, R. et al. (1987) Embo J. 6: 3901–3907
Loyd,A. et al (1992), Science 258, 1773–1775
Murashige, T. and Skoog, F. (1962) Physiol. Plant. 15: 73–97
Sambrook, J. et al. (1989) Molecular Cloning. A laboratory manual. Cold Spring Harbor Laboratory Press, Cold Spring Harbor, N.Y.
Saul, M. W. et al. (1988) Plant Mol. Biol. Man. Al: 1–16 (Eds.
Gelvin S. B. and Schilperoort, R. A.) Kluwer Academic Pubs., London
Symmans et al (1990) Biotechnology 8, 217–221
Vancanneyt, G. et al (1990). Mol. Gen. Gen. 220, 245–250.
Van Engelen, F. et al. (1995) Transgenic R. 4: 288–290
VanTunen, A. J. et al. (1988) EMBO J. 7: 1257–1263

EXAMPLES

Example 1

Plant Material

Plants of tomato line FM6203 and transformants are grown in soil in a glasshouse with a 16 hour photoperiod and a 23/18° C. day/night temperature.

Example 2

Bacterial Strains

The *Escherichia coli* strain used is:
DH5α supE44, (lac ZYA-ArgF)U169, 80lacZM15, hsdR17 (rk–, mk+), recA1, endA1, gyrA96, thi-1, relA1, deoR (Hanahan, 1983).

The Agrobacterium strain used is LBA4404 (Hoekema, 1985).

Transformation of *E. Coli* DH5α is performed using the method of Hanahan, (1983).

Transformation of Agrobacterium LBA4404 is performed using a freeze/thaw method according to Saul et al, (1988).

Example 3

Elucidation of the Rate-limiting Step in Flavonol Production in Tomato Fruit

The rate-limiting step in flavonol production in tomato fruit is determined using two complimentary approaches; high performance liquid chromatography (HPLC) analysis of flavonoids in ripening tomato fruit and northern analysis using probes for the flavonoid biosynthetic genes chalcone synthase (chs), chalcone isomerase (chi) and flavonol synthase (fls).

3.1 Analysis of Flavonoids in Ripening Tomato Fruit by HPLC 3.1.1 Harvest of Tomato Fruit Tomato fruit are harvested at five stages of ripening (green, breaker (the ripening stage corresponding to the appearance of the first flush of color on the green fruit), turning, red and over-ripe; corresponding to approximately 21, 28, 31, 46 and 55 days post anthesis respectively). For discrimination between flavonoids in peel and flesh tissues, the outer layer of approximately 2 mm thick (i.e. cuticula, epidermal layer plus some sub-epidermal tissue) is separated from the fruit using a scalpel and classified as peel. The jelly and seeds are then removed and the remainder of the fruit is classified as flesh tissue. After separation, tissues are quickly cut into pieces and frozen in liquid nitrogen before being ground into a fine powder using a pre-cooled coffee grinder. Peel and flesh tissues are lyophilised for 24 hr and then stored under desiccating conditions at 40C until use.

3.1.2 Extraction of Flavonoids from Tomato Tissues

Determination of flavonoid glycosides and narichalcone (2',4',6',4-tetrahydroxychalcone) in tomato fruit is carried out using a non-hydrolysing method as follows: 40 mg of freeze-dried tomato tissue is weighed and transferred to a 10 ml Pyrex glass tube. To each tube 4 ml of 75% aqueous methanol acidified with HCl to pH 2 is added. The tubes are closed with screw tops containing a Teflon inlay and incubated at room temperature (20–25° C.) for 1 hr with continuous mixing on a roller band.

3.1.3 High Performance Liquid Chromatography (HPLC) Conditions for Flavonoid Analysis 1 ml of each tomato fruit extract is taken using a disposable syringe and filtered through a 0.2 µm PTFE disposable filter (Inacom Instruments BV, The Netherlands) before injection into the HPLC system.

The HPLC system consisted of a Waters 600E Multisolvent Delivery System (Waters Chromatography), a Promis autoinjector (Separations Analytical Instruments BV) with a fixed 10 µl loop, and a Nova-Pak $C_{18}$ (3.9×150 mm, particle size 4 µm) analytical column (Waters Chromatography) protected by a Guard-Pak Nova-Pak C18 insert. Both columns are placed in a LKB 2155 HPLC column oven (Pharmacia Biotech) set at 30° C. A photodiode array detector (Waters 996) is used to record spectra of compounds eluting from the column on-line. The detector is set at recording absorbance spectra from 240 to 600 nm with a resolution of 4.8 nm, at a time interval of 1 sec. Millennium 2010 Chromatography Manager (Waters Chromatography BV) is used to control the solvent delivery system and the photodiode array detector.

HPLC separation of flavonoids in non-hydrolysed extracts is performed using a gradient of acetonitril in 0.1% TFA, at a flow rate of 1 ml/min: 12.5–17.5% linear in 3 min, then 17.5–25% in 32 min and 25–50% in 2 min, followed by a 3 min washing with 50% acetonitril in 0.1% TFA. After washing, the eluent composition is brought to the initial condition in 2 min, and the column is equilibrated for 6 min before the next injection.

HPLC data are analysed using the software of the Millennium 2010 Chromatography Manager. Absorbance spectra (corrected for baseline spectrum) and retention times of eluting peaks (with peak purity better than purity threshold value) are compared with those of commercially available flavonoid standards. Quercetin and kaempferol glycosides and narichalcone are quantified based on absorption at 360 nm. Dose-response curves (0 to 20 µg/ml) were established to quantify these compounds in the non-hydrolysed tomato extracts. Flavonoid levels in tomatoes are calculated on a dry weight basis for peel and flesh tissues. With the HPLC system and software used, the lowest detection limit for flavonoids in tomato extracts is about 0.1 µg/ml, corresponding with 10 mg/kg dry weight and 1 mg/kg fresh weight. Variation between replicate injections is generally less than 5%.

3.1.4 Characterisation of the Flavonoid Content in Ripening Tomato Fruit

Two dominant flavonoids are detected in the peel of ripe tomato fruit, the flavonol rutin (quercetin 3-rutinoside) and narichalcone, which are identified by their retention time (RT) and absorbance spectrum. At least four other flavonol glycosides are also identified in the tomato peel extracts, albeit in much smaller quantities than rutin or narichalcone. A full identification of these minor flavonol glycoside species is described in Example 8.

In contrast, the flesh tissue from ripe tomato fruit contains only traces of rutin, no other flavonoid species are detectable.

Figure 1B:
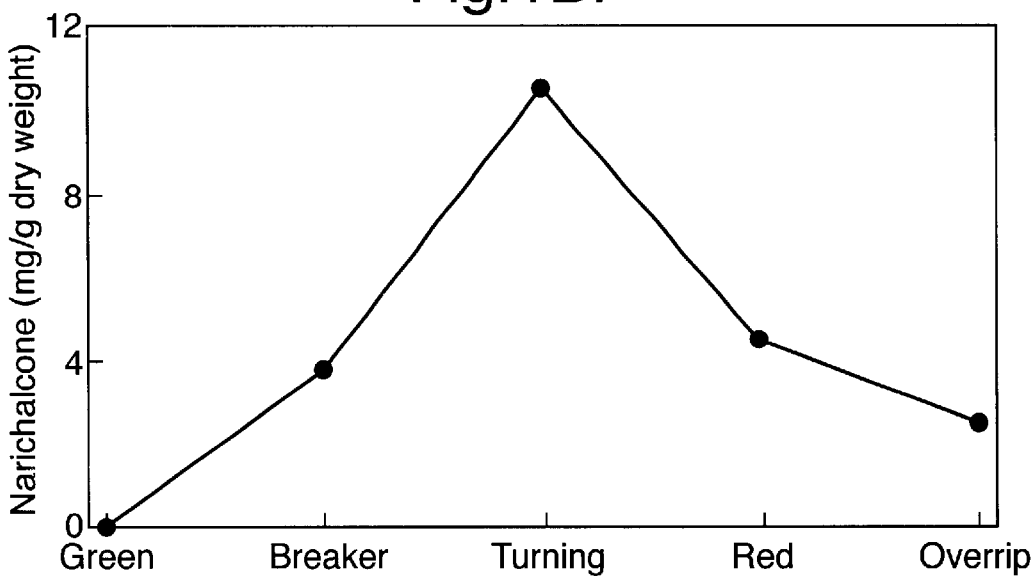
Figure 10:
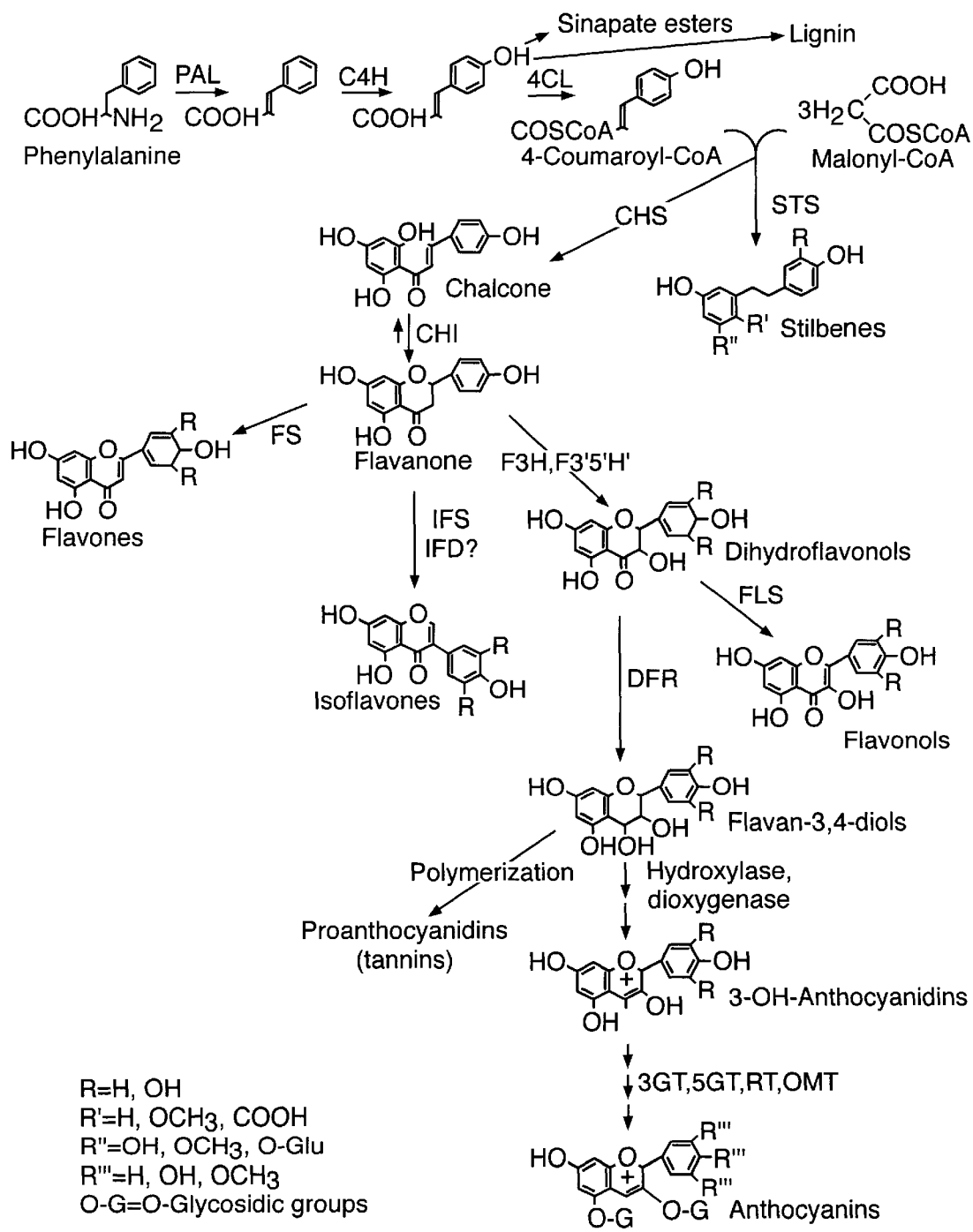
FIG. 10 shows the proposed biosynthetic pathway for the production of flavonoids.

The levels of rutin and narichalcone in the peel during ripening of tomato fruit are shown in FIG. 1. Rutin levels increase during tomato ripening reaching their highest levels in the over-ripe stage (approximately 1 mg/g dry weight of peel). Narichalcone is absent in the peel of green fruit but increases sharply during coloring of the fruit, reaching levels of approximately 10 mg/g dry weight in peel of turning fruit before declining through the red and over-ripe stages. The enzyme chalcone isomerase (CHI) is believed to be responsible for catalysing the formation of naringenin from narichalcone in the flavonoid biosynthetic pathway (FIG. 10). Applicants are of the opinion that the accumulation of narichalcone suggests that in the peel of ripening tomatoes CHI represents a rate limiting enzyme in the formation of flavonols.

3.2 Northern Analysis of Ripening Tomato Fruit

Northern analysis is used to determine the endogenous expression of the flavonoid biosynthetic genes chs, chi and fls during the development of FM6203 tomato fruit.

RNA is isolated from the peel and flesh of green, breaker, turning and red fruit and also young leaves according to the protocol of van Tunen (1988). For RNA gel blot analysis, 10 µg of RNA is loaded on formaldehyde agarose gels and electrophoresed overnight at 25V. Separated RNA is then blotted overnight onto Hybond $N^+$ membrane (Amersham).

*Petunia hybrida* cDNA fragments encoding the following flavonoid biosynthetic enzymes are used as probes: chalcone synthase (CHS-A), chalcone isomerase (CHI) and flavonol synthase (FLS). These fragments are obtained by RT-PCR on RNA extracted from closed flowers of *Petunia hybrida* W115 with primer combinations F15/F16 (chi-a), F13/F14 (chs-a) and F20/F21 (fls). The obtained PCR products are checked by sequence analysis.

Probes are labelled with 32P and purified according to methods given in Gibco Life Technologies RadPrime Labelling system. Blots are hybridised overnight at 55° C. and washed three times in 2×SSC, 0.1% SDS, 55° C., 30 min, before being exposed to X-ray film for 48 hr.

The results of the northern blot are shown in FIG. 2. Both the chs and fls transcripts are abundantly present in the peel of tomato fruit in all developmental stages tested. The level of these two transcripts peaks during the breaker and turning stage of development and subsequently decreased in the red stage. The chi transcript level is very low in the peel of all developmental stages. Without wishing to be bound by any theory, applicants believe that this is indicative that one of the rate limiting steps in flavonoid biosynthesis in the peel may lie at the level of chi gene expression. This result is in agreement with the observation that narichalcone (the substrate for CHI), accumulated to high levels in breaker and turning stage fruit (Example 3.1).

In the flesh of tomato fruit, the levels of chs, chi and fls transcripts are very low, in agreement with the HPLC data which showed only trace amounts of rutin in this tissue (Example 3.1).

Chs, chi and fls transcripts are present in low but detectable levels in tomato leaves.

Example 4

Gene Constructs 4.1 Strategy to Overexpress a Rate-liming Step of Flavonol Production in Tomato Fruit During the early stages of ripening of tomato fruit narichalcone accumulates in the peel of the fruit (Example 3.1). The enzyme responsible for converting narichalcone into naringenin is CHI. The expression levels of the gene encoding CHI remain low throughout ripening of the fruit (Example 3.2) suggesting CHI may constitute a rate-liming step in the production of flavonols in the peel of tomato fruit.

The strategy consists of increasing the production of flavonols in tomato fruit by overexpression of the *Petunia hybrida* gene encoding CHI. The introduced gene is expressed under the control of the constitutive enhanced CaMV 35s promoter (also called double P35s or Pd35S).

4.1 Cloning the chi Gene from *Petunia hybrida*

The chi-a gene is amplified from plasmid pMIP41, which contains the complete chi-a cDNA from *Petunia hybrida* inbred line V30 (Van Tunen et al. 1988), with primer combination F15/F16. These primers contain a 5' extension with a unique BamHI (F15) and SalI (F16) restriction site (Table 1). This results in a 0.73 kb chi-a fragment.

4.2 Construction of the chi Gene Fusion

Figure 3:
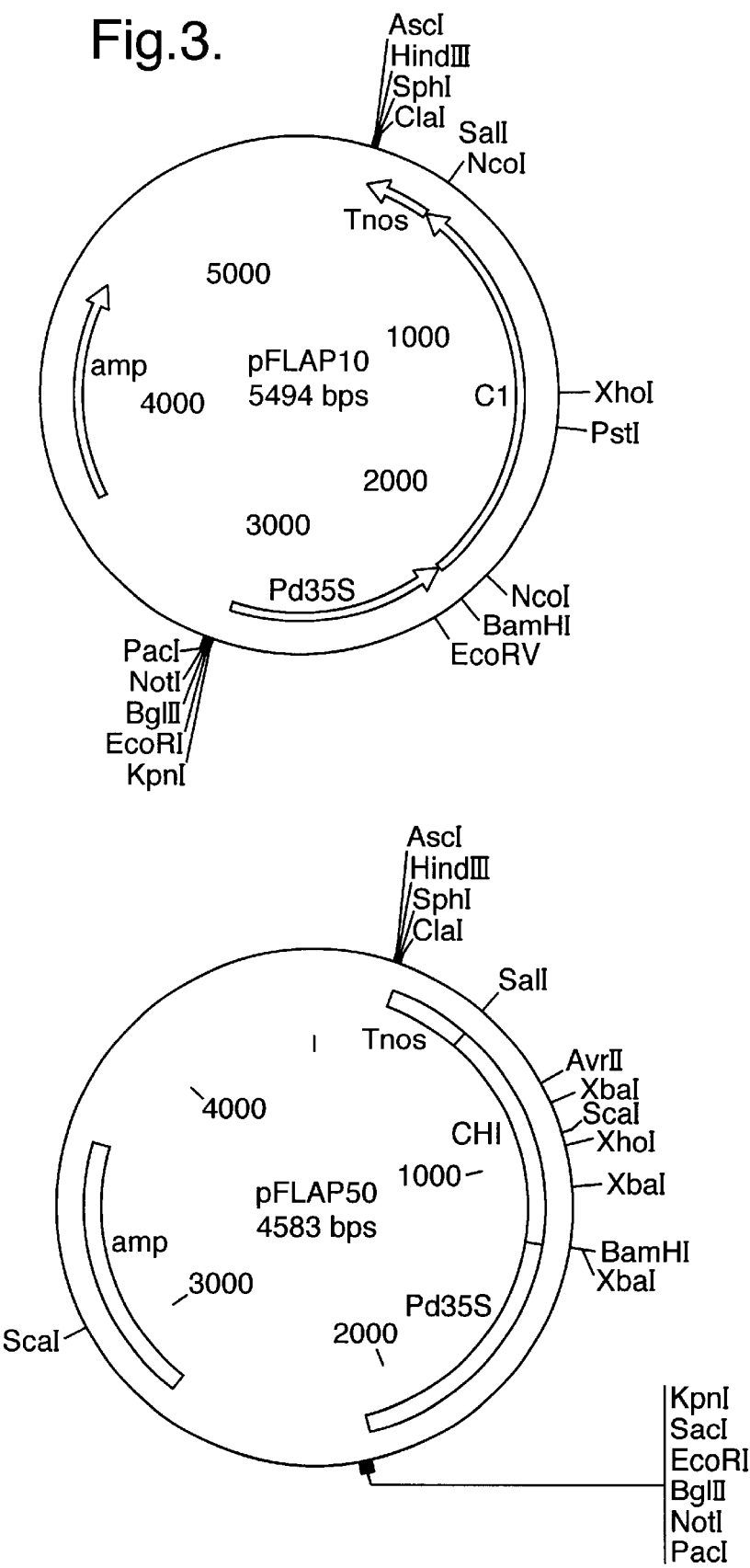
FIG. 3 shows the restriction maps of pFLAP10 and pFLAP50.

The Pd35S-chi-Tnos gene construct is made as follows. Plasmid pFLAP10, a pUC-derivative containing a fusion of the consitutive enhanced CaMV 35s promoter (P35s), the maize c1 gene (c1) and the *Agrobacterium tumefaciens* nos terminator (Tnos), is used as recipient of the chi-a gene (FIG. 3a). A description of the properties of plasmid pFLAP10 is given in FIG. 3. The amplified chi-a cDNA is digested with BamHI/SalI and the resulting 730 bp fragment is ligated in plasmid pFLAP10 digested with the same enzymes, thus replacing the cl gene with the chi-a gene. The resulting plasmid is denoted pFLAP50 (FIG. 3b).

4.2.1 Construction of pFLAP10

Figures 13, 14:
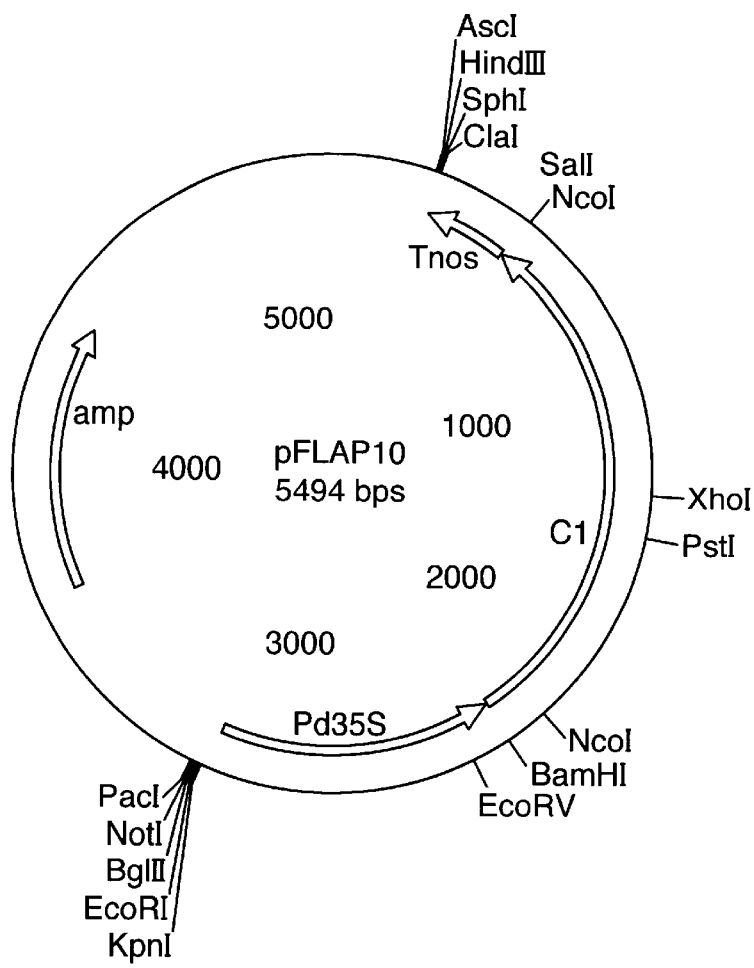
FIG. 13 shows the restriction map of plasmid pFLAP10.
FIG. 14. shows the multiple cloning site as altered in pUCM2 from AscI to PacI in the 5' to 3' orientation.

The $C_1$ gene fusion was cloned in plasmid pUCM2, a derivative of plasmid pUCAP (Van Engelen et al. 1995, Transgenic Research 4, p. 288–290), in which the multiple-cloning-site was altered (FIG. 12), in three major steps. Said altered multiple cloning site is shown in FIG. 14.

Firstly, Tnos was amplified by PCR from pBI121 with primers F12 and AB13 (see Table 1). The resulting 250 bp product was cloned in pUCM2 as a SalI/ClaI fragment. This resulted in plasmid pFLAP1.

Secondly, the cl gene was cloned as a BamHI/SalI fragment upstream of Tnos in pFlap2 as follows. The c1 gene was transferred as a 2 kb EcoRI fragment from plasmid pAL77 (Loyd 1992) to high-copy plasmid pBluescript SK−, resulting in plasmid pBlC1. The c1 gene was isolated from pBlC1 as a 1.6 kb EcoRI/PacI fragment and adapters F7F8 and F9F10 (Table 1) were ligated to each end of the fragment in order to add unique BamHI and SalI restriction sites on both ends of the gene and to destroy the EcoRI and PacI sites. The resulting BamHI/SalI c1 fragment was cloned upstream of the nos terminator, resulting in plasmid pFLAP2.

Thirdly, Pd35s was cloned as a KpnI/BamHI fragment upstream of c1 in pFLAP2 as follows. To create a unique BamHI site at the 3' end of the d35s promoter, plasmid pMOG18 (Symans et al 1990, Biotechnology 8, p. 217–221) was digested with EcoRV/BamHI, thus removing the 3' part of the d35s promoter and the gusA gene. The 3' part of the 35s promoter present in plasmid pAB80 (Bovy et al. (1995)) was ligated as a 0.2 kb EcoRV/BamHI fragment in the pMOG18 vector, resulting in plasmid pMOG18B. To create a unique KpnI site at the 5' end of the d35s promoter plasmid pMOG18B was digested with EcoRI, the ends were polished with Klenow polymerase, and a subsequent digest with BamHI was done. The resulting 0.85 kb blunt/BamHI d35s promoter fragment was cloned into plasmid pBlC1 followed by digestion with XhoI and polished with Klenow polymerase/BamHI. This resulted in plasmid pBld35S. Finally the d35s promoter was transferred as a KpnI/BamHI fragment from pBld35s to plasmid pFLAP2. This resulted in plasmid pFLAP2 (FIG. 13).

4.3 Construction of Binary Vector pBBC3

Figure 4:
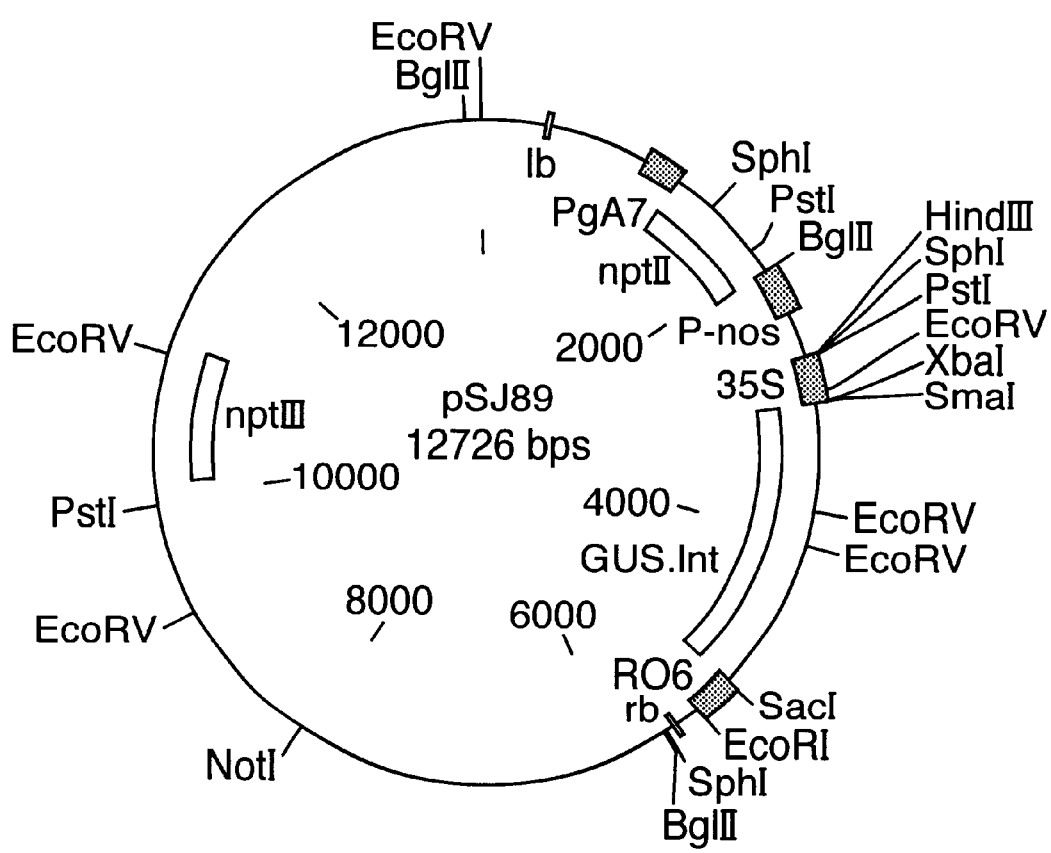
FIG. 4 shows the restriction maps of pBBC3, pBBC50 and pSJ89.

To obtain a binary vector with suitable cloning sites to transfer the chi gene fusion into, plasmid pBBC3, a derivative of PGPTV-KAN (Becker et al. (1992) is constructed as follows. Synthetic adapter F38F39 (Table 1) is ligated in plasmid pGPTV-KAN digested with EcoRI/HinDIII. In this way the gusA-Tnos gene in pGPTV-KAN is replaced by a small multiple-cloning-site consisting of PacI/EcoRI/HinDIII/IAscI restriction sites (FIG. 4a).

4.4 Transfer of the chi Gene Fusion into pBBC3

The Pd35s-chi-Tnos insert is transferred from pFLAP50 as a PacI/AscI fragment into binary vector pBBC3, digested with the same enzymes. The resulting binary plasmid is denoted pBBC50 (FIG. 4b).

4.5 GPTV Control Plasmid

A GPTV-based binary plasmid (pSJ89) containing the β-glucuronidase gene (with the st-ls1 intron; Vancanneyt et al. 1990) under control of the CaMV 35s promoter and the nos poly(A) signal (P35s-gusA-Tnos) is used as a control plasmid to transform FM6203 (FIG. 4c). This allows direct comparison between gus transformed control plants and plants containing the chi construct as both sets of plants have gone through the tissue culture procedure.

Plasmid pSJ89 is constructed as follows: the CaMV 35s promoter-gus-int fragment (Vancanneyt et al, 1990) is cloned as a HindIII-SacI fragment into the same sites of plasmid pSJ34, a derivative of the binary vector pGPTV-KAN (Becker et al, 1992) in which the BamHI site between the NPTII selectable marker and the gene 7 poly(A) signal is destroyed by filling in with klenow polymerase.

Example 5

Stable Transformation of chi Construct into Tomato Line FM6203

5.1 *Agrobacterium tumefaciens* Transformations

Binary plasmids pBBC50 and pSJ89 are introduced into Agrobacterium strain LBA4404 by adding 1 μg of plasmid DNA to 100 μl of competent Agrobacterium cells, prepared by inoculating a 50 ml culture in YEP medium (Sambrook, 1989) and growing at 28° C. until the culture reaches an $OD_{600}$ of 0.5–1.0. The cells are then pelleted, resuspended in 1 ml of $CaCl_2$ solution and dispensed into 100 μl aliquots. The DNA-Agrobacterium mixture is frozen in liquid nitrogen and thawed in a water bath at 37° C. After the addition of 1 ml YEP medium the bacteria are incubated at 28° C. for 4 hours with gentle shaking. Finally transformed bacteria are selected on YEP-agar plates containing 50 μg/ml kanamycin. The presence of the plasmids is tested by PCR analysis using pBBC50 (chi 5 and nos ant) or pSJ89 (300 35s and gus 2) specific primers respectively (Table 1).

5.2 Tomato Transformations

Seeds from tomato line FM6203 are sterilised by a 2 h incubation in 1.5% hypochlorite, followed by three rinses of sterile water. The seeds are germinated and seedlings are grown for 8 days on a 1:1 mixture of vermacolite and MS medium (Murashige and Skoog, 1962; Duchefa) supplemented with 0.3% (w/v) sucrose, with a photoperiod of 16 h (3000 lux) at 25° C.

Eight-day old cotyledons are cut into 25 mm squares and preincubated for 24 h on tobacco suspension feeder layer plates at low light intensity (1000 lux). The tobacco leaf suspension culture is grown on plates containing MS medium including vitamins, supplemented with sucrose (3% w/v), agarose (6 g/l), 2,4-dichlorophenoxyacetic acid (2,4-D; 0.5 mg/l) and benzylaminopurine (BAP; 0.5 mg/l).

A single colony from the Agrobacterium LBA4404 cultures containing one of the binary vectors mentioned in Example 4.4 and 4.5 is grown for 48 h in liquid Minimal A medium (Sambrook, 1989) supplemented with 50 μg/ml kanamycin to an $OD_{600}$ of 0.5–1.0. The bacteria are pelleted by centrifugation and resuspended in MS medium including vitamins (Duchefa) and 3% (w/v) sucrose at an $OD_{600}$ of 0.5. The cotyledon explants are incubated in the Agrobacterium suspension for 30 min, blotted dry on filter paper and co-cultivated for 48 h on tobacco feeder layer plates at 25° C. and low light intensity.

After co-cultivation, the explants are transferred to regeneration medium, consisting of MS medium supplemented with Nitsch vitamins, sucrose (2% w/v), agargel (5 g/l), zeatin-riboside (2 mg/l), kanamycin (100 mg/l) and cefotaxime (500 mg/l). Regenerating explants are transferred to fresh medium every two weeks. Regenerating kanamycin resistant shoots were transferred to rooting medium, consisting of MS medium plus B5 vitamins, supplemented with sucrose (0.5% w/v), gelrite (2 g/l), kanamycin (50 mg/l) and cefotaxime (250 mg/l). During regeneration and rooting explants are incubated in a growth chamber at 25° C. with a 16 h photoperiod (3000 lux). After root formation, the presence of the CHI insert is confirmed by PCR analysis of cotyledon tissue using specific primers (chi 5 and nos ant), and the presence of the GUS insert using 300 35s and gus2 specific primers (Table 1). PCR positive plantlets are transferred to soil and grown in the greenhouse.

Transgenic plants carrying the construct pBBC50 are numbered from C6 onward. Control transgenic plants carrying the construct pSJ89 are numbered from G2 onward.

Example 6

Southern Analysis of Transgenic Plants

The presence and the copy number of the transgenes is determined in transgenic plants by southern hybridisation. Genomic DNA is isolated from young leaves as described by Fulton et al., (1995). Aliquots of 10 µg genomic DNA are digested for 16 h with EcoRI and separated on a 0.8% TAE agarose gel. The DNA is denatured in 0.5 M NaOH, 1.5M NaCl for 45 min before being transferred to a Hybond N+ membrane (Amersham) in 20×SSC.

The blots are probed with a 700 base pair P radiolabeled nptII-specific PCR fragment, amplified from plasmid pBBC3 with primers npt IIa and npt IIb (Table 1), under stringent conditions (65° C.).

Prehybridisation is carried out for 2 h at 65° C. in a mix of 0.5 M $Na_2PO_4$ pH 7.2, 7% SDS. and 0.1 mg/ml denatured herring sperm DNA. Hybridisation is performed by adding denatured probe DNA to the prehybridisation medium and, continuing the incubation at 65° C. for 16 h. The hybridised blots are washed once for 30' at 25° C. in 2×SSC, 0.1% SDS and then once for 30' at 65° C. in 2×SSC, 0.1% SDS before being autoradiographed.

Figure 5:
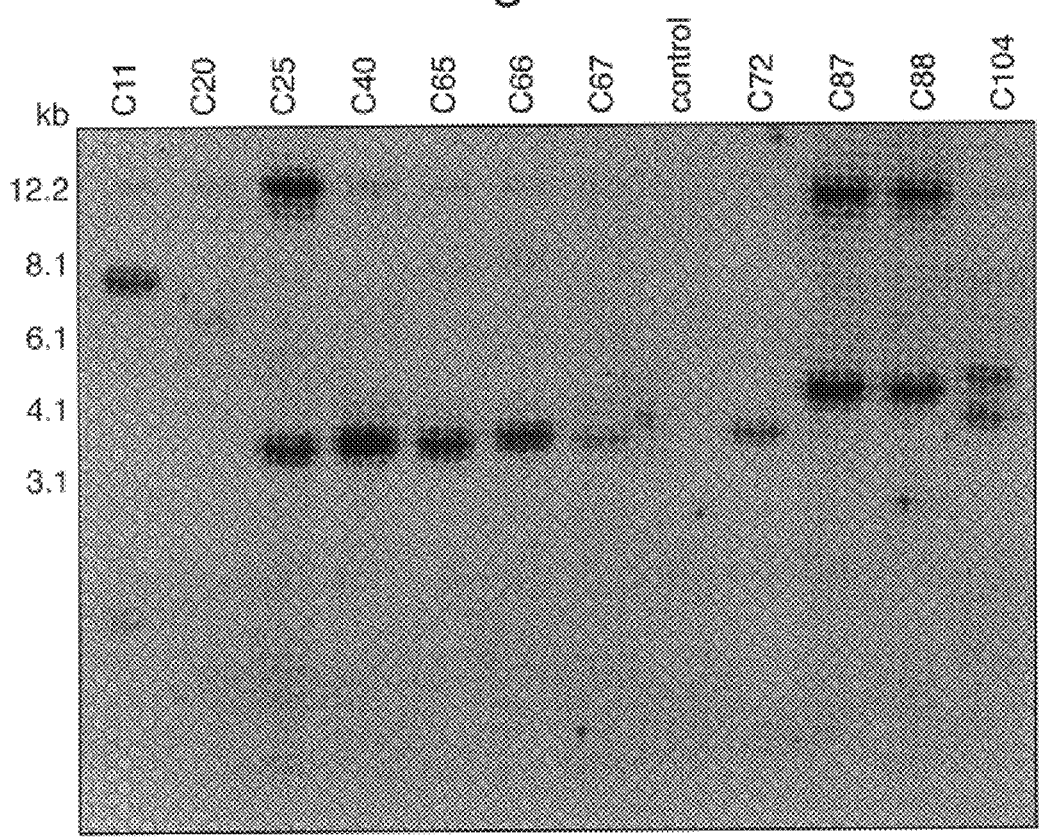
FIG. 5 shows the Southern blot of chromosomal DNA from tomato. Chromosomal DNA was isolated from young leaves of transgenic and non-transgenic tomato plants. 10 μg DNA was digested with EcoRI, separated on an agarose gel and blotted onto a nylon filter. The DNA was hybridised with a $^{32}$P-labelled nptII specific probe and autoradiographed.

The result of the southern analysis is shown in FIG. 5. The control is an untransformed FM6203 plant. Southern analysis confirms the initial screening of transgenics by PCR (see Example 5.2), every pBBC50 transformed plant hybridised with the npt II probe. Transgenic plants contain either 1 or 2 copies of the insert.

Example 7

Measurement of Flavonoids in Transformed Tomato Plants 7.1 Growth and Harvest of Tomato Fruits Transgenic tomato plants are grown in 10 1 pots in a glasshouse at standard growth conditions (day/night temperatures 23° C./18° C., 16 hr light)). Fruits are harvested between 15–21 days post-breaker stage (corresponding to fully red ripe fruit). For discrimination between flavonoids in peel and flesh tissues, the outer layer of approximately 2 mm thick (i.e. cuticula, epidermal layer plus some subepidermal tissue) is separated from the fruit using a scalpel and classified as peel. The jelly and seeds are then removed and the remainder of the fruit was classified as flesh tissue. After separation, tissues are quickly cut into pieces, frozen in liquid nitrogen and stored at −80° C. until use.

7.2 Extraction of Flavonoids from Tomato Tissues

Flavonoids are determined as aglycons or as their glycosides by preparing hydrolysed and non-hydrolysed extracts, respectively.

Acid hydrolysis is used as an initial screen of transformants in order to identify those lines containing high amounts of flavonols as compared to the control. Acid hydrolysis ensures that flavonoid glycosides such as rutin and kaempferol rutinoside are hydrolysed to their respective aglycones i.e. quercetin and kaempferol.

Preparation of hydrolysed extracts is performed according to Hertog et al (1992) with some modifications. Frozen tissues are ground into a fine powder using a pre-cooled coffee grinder. Peel and flesh tissues are lyophilised for 24 h before flavonoid extraction. 50 mg of this freeze-dried material was weighed and transferred to a 6 ml Pyrex glass tube. To each tube 1.6 ml of 62.5% methanol (HPLC grade) in distilled water and 0.4 ml of 6 M HCl are added. The tubes are closed with screw caps containing a Teflon inlay and incubated for 60 min at 90° C. in a waterbath.

After hydrolysis, the tubes are cooled on ice, the extracts are diluted with 2 ml of 100% methanol and sonicated for 5 min. 1 ml of the sample was then filtered over a 0.2 µm PTFE disposable filter into a standard 1.8 ml HPLC vial.

Preparation of non-hydrolysed extracts is performed as follows: Frozen tissues are ground to a fine powder using a pre-cooled coffee grinder. Peel and flesh tissues are lyophilised for 24 h before flavonoid extraction. 50 mg of freeze dried material is weighed and transferred to a 6 ml Pyrex glass tube. 4 ml of 70% methanol (HPLC grade) in distilled water is added to each tube. The tubes are closed with screw top caps containing a Teflon inlay and placed in a sonicating water bath at room temperature for 30 min. After sonication 1 ml of the sample is filtered over a 0.2 µm PTFE disposable filter into a standard 1.8 ml HPLC vial.

7.3 HPLC Conditions for Flavonoid Analysis

Chromatography of samples is performed using a chromatography station equipped with a dual pump system and automated gradient controller (model 1100; Hewlett Packard), a Waters auto-injector (model 717) with a variable 20 pl loop and a Nova-Pak $C_{18}$ (3.9×150 mm, particle size 4 µm) analytical column (Waters Chromatography) protected by a Guard-Pak Nova-Pak C18 insert. Both columns are placed in a LKB 2155 HPLC column oven (Pharmacia Biotech) set at 30° C. A photodiode array detector (model 1040M, Hewlett Packard) is used to record spectra of compounds eluting from the column on-line. The detector is set at recording absorbance spectra from 240 to 600 nm with a resolution of 4.8 nm, at a time interval of 1 second. Peak purity, identification and integration were carried out on Hewlett Packard Chemstations software version A.04.02.

HPLC separation of flavonoids present in hydrolyzed extracts (flavonols and naringenin) is carried out under isocratic conditions of 25% acetonitril (for HPLC far UV) in 0.1% trifluoroacetic acid (TFA) at a flow rate of 0.9 ml/min.

HPLC separation of flavonoids in non-hydrolysed extracts (flavonoid-glycosides and narichalcone) is performed using a gradient of acetonitril in 0.1% TFA, at a flow rate of 1.0 ml/min: 5–25% linear in 30 min, then 25–30% in 5 min and 30–50% in 2 min followed by a 3 min washing with 50% acetonitril in 0.1% TFA. After washing, the eluent composition is brought to the initial condition in 2 min, and the column is equilibrated for 6 min before next injection.

HPLC data are analysed using the software of the Hewlett Packard Chemstations software version A.04.02. Absorbance spectra (corrected for baseline spectrum) and retention times of eluting peaks (with peak purity better than purity threshold value) are compared with those of commercially available flavonoid standards. Quercetin and kaempferol aglycons are detected and calculated from their absorbance at 370 nm, naringenin at 280 nm and flavonolglycosides as well as narichalcone at 360 nm. Flavonoid levels in tomatoes are calculated on a dry weight basis. With the HPLC system and software used, the lowest detection limit for flavonoids in tomato extracts is about 0.1 $\mu$g/ml, corresponding with 10 mg/kg dry weight and 1 mg/kg fresh weight.

Using flavonoid standards (obtained from Apin Chemicals Ltd, Abingdon, UK) it is established that during the hydrolysis step, aglycons are released from their respective glycosides for 100%, while chemically converted into naringenin for more than 95%. Recoveries of quercetin, kaempferol and naringenin standards added to peel or flesh extracts just before hydrolysis are more than 90%.

Example 8

Figure 6A:
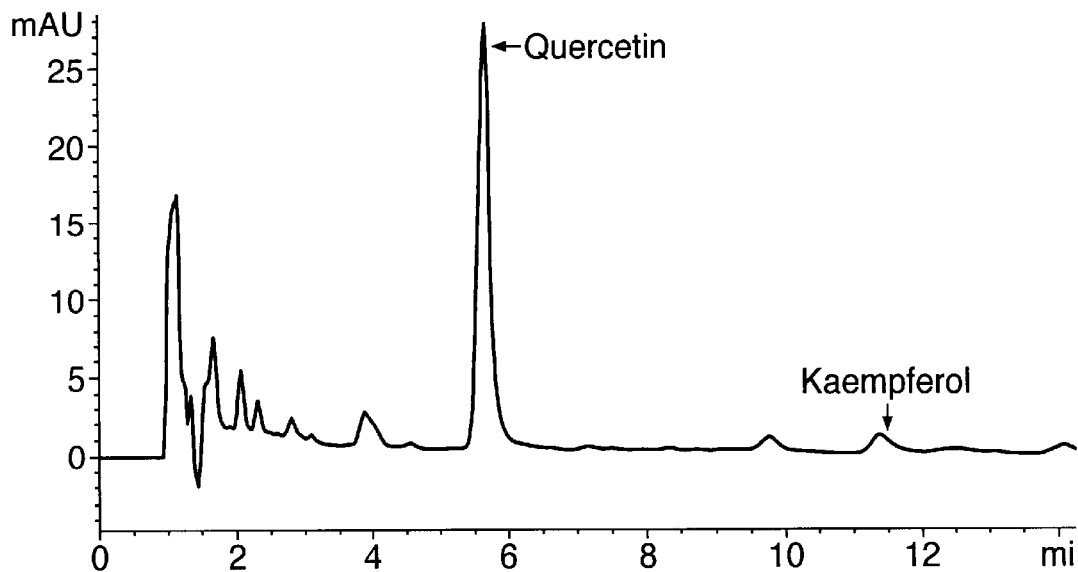
FIGS. 6A–6B shows typical HPLC chromatograms, recorded at 370 nm, of hydrolysed extracts of (A.) peel and (B.) flesh tissue of plants transformed with the control plasmid pSJ89. Peaks corresponding to the quercetin and kaempferol aglycons are indicated.
Figure 6B:
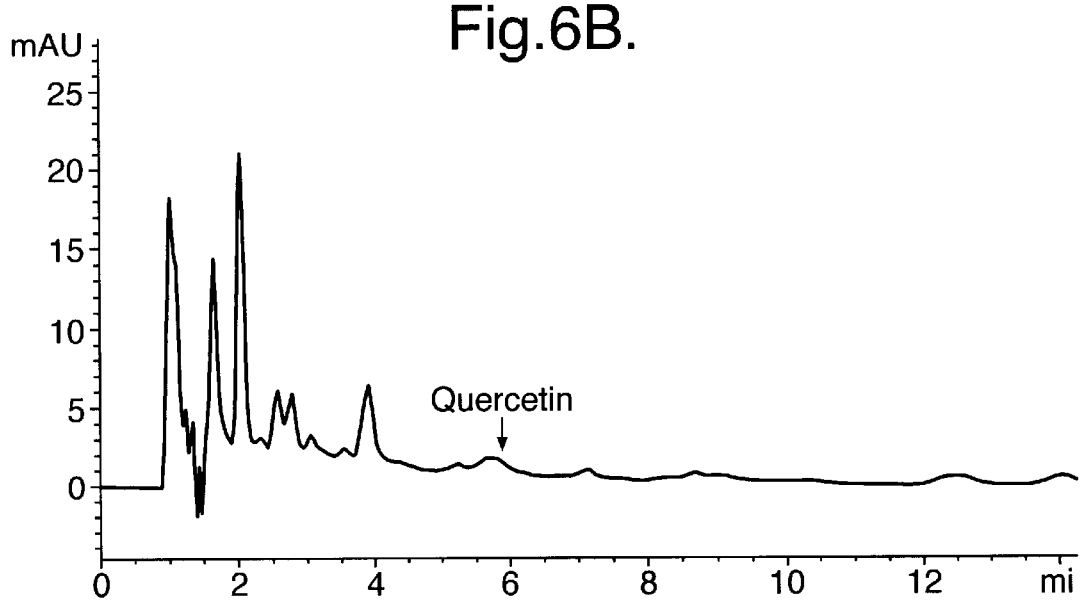

Characterisation of the Flavonoid Content in Transgenic Tomato Fruit 8.1 Flavonoids in Peel and Flesh of Control Tomatoes In hydrolysed extracts of control red fruit of variety FM6203 transformed with pSJ89, both quercetin and kaempferol are present in peel tissue (FIG. 6a). In contrast, the hydrolysed extracts of flesh tissue from this fruit contain only traces of quercetin with no detectable levels of kaempferol (FIG. 6b). Without wishing to be bound by any theory, applicants believe that the small amount of quercetin detected in the hydrolysed extracts of flesh originates from the vascular tissue in the flesh. Chromatograms obtained at 280 nm (not shown) of the same extracts reveal a large peak of naringenin in the peel, but not in the flesh. There is no significant difference in the identity and quantity of flavonoids found in the control pSJ89-transformed tomatoes and those found in untransformed tomatoes (data not shown.

In non-hydrolysed extracts of control tomatoes transformed with pSJ89, at least 5 different flavonol-glycosides as well as narichalcone are detected in the peel (FIG. 7). NMR-studies (not shown) prove that the peak at RT=16.9 min is rutin while the peak at 15.2 min is a quercetin-3-trisaccharide: rutin with apiose linked to the glucose of the rutinoside. The retention time and absorbance spectrum of the minor peak at 17.3 min correspond with those of quercetin-3-glucoside, while those of the peak at 19.7 min correspond with kaempferol-3-rutinoside. The small peak at 20.4 min has an absorbance spectrum comparable to kaempferol-3-rutinoside, but its higher RT value indicates a yet unknown kaempferol-glycoside. The large peak at 33.2 min is narichalcone. Aglycons of quercetin and kaempferol, as well as naringenin (all present in hydrolysed peel extracts) are not detectable in any of the non-hydrolysed extracts. In the non-hydrolysed flesh sample only a small peak corresponding to rutin is detected (data not shown).

After comparing the flavonoid species in hydrolysed extracts with those in non-hydrolysed extracts of the same tissue, we conclude that the presence of quercetin and kaempferol aglycons in the hydrolysed extracts results from hydrolysis of their respective glycosides; the presence of naringenin in hydrolysed peel extracts results from isomerization of narichalcone during the hydrolysis step (cf. Example 7.3).

8.2 Flavonoids in Fruits of Transformed Tomato Plants

To determine whether the pBBC50 construct was able to overcome the suspected rate limiting step in flavonol production in tomato fruit, transformants are analysed for the presence of flavonoids in the flesh and peel of their fruits. This screening is performed by HPLC using hydrolysed extracts. Thirty six independent plants transformed with pBBC50, as well as six control plants transformed with pSJ89 are analysed.

Analysis of hydrolysed extracts of flesh samples from pBBC50 transformed fruit reveals no significant increase in flavonoids compared to the control pSJ89 fruit (FIG. 8). The differences in quercetin concentration in tomato flesh that are shown in FIG. 8 are believed to be within the experimental error. Said experimental error is believed to be relatively high when working at low concentration near the detection limit of 20 $\mu$g/g DW flesh.

Figure 11:
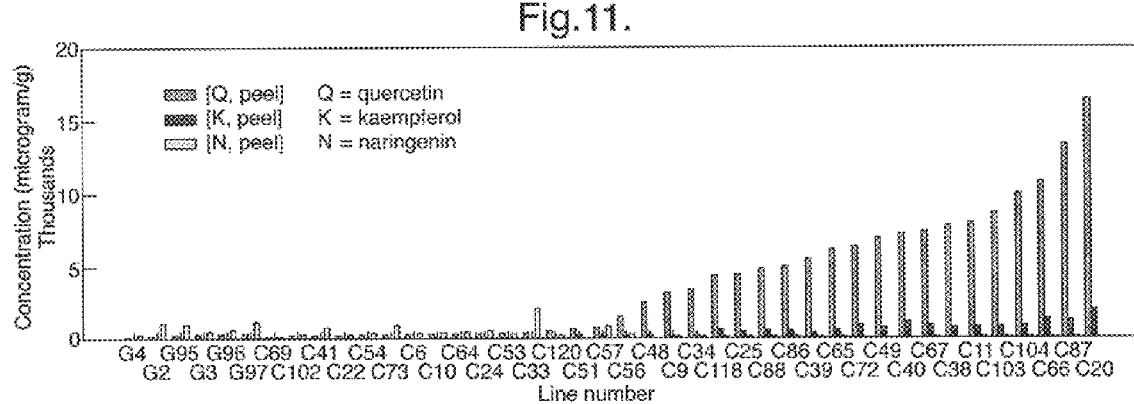
FIG. 11 shows the graph of the data represented in table 2.

In contrast, analysis of the hydrolysed extracts of peel of the tomato fruit reveals that the presence of the pBBC50 construct results in a significant increase in the levels of both quercetin and kaempferol type flavonols in a proportion of transformed plants (Table 2, FIG. 11). Hydrolysed extracts of pBBC50 transformed plants display a range of peel quercetin concentrations with one line expressing a 69 fold increase over the pSJ89 transformed control lines (plant C20). The amount of kaempferol present in the hydrolysed extracts of pBBC50 transformed plants correlates with their quercetin concentrations—lines with higher concentrations of quercetin seem also to possess higher concentrations of kaempferol in hydrolysed extracts of their peel. Applicants wish to point out that the variety in concentrations of quercetin, kaempferol and naringenin as measured for the transformed plants is believed to represent the common representation of a transgenic population. Applicants however wish to stress that the currently obtained data clearly show an increase in the level of quercetin and kaempferol in the peel of transformed plants.

The pBBC50 transformed plants also display a range of peel naringenin concentrations (note that these measurements were carried out on hydrolysed extracts, therefore the naringenin was originally derived from narichalcone as can be deduced from analysis of non-hydrolysed extracts cf. Example 8.1). In general, those transformants possessing increased concentrations of flavonols in their peel also possess decreased concentrations of naringenin when compared to the control fruit (Table 2). That the decrease in naringenin concentrations correlates with an increase in flavonol concentrations in the peel of the pBBC50 transformed fruits strongly suggests that CHI no longer represents a rate-limiting step in these plants.

The significant increase in fruit flavonol levels seen in the pBBC50 transformed plants seems to reveal that, as suggested in Example 2, CHI represents a major rate limiting step in the production of flavonols in tomato peel which has now been overcome by the heterologous expression of the petunia chi gene.

Figure 9:
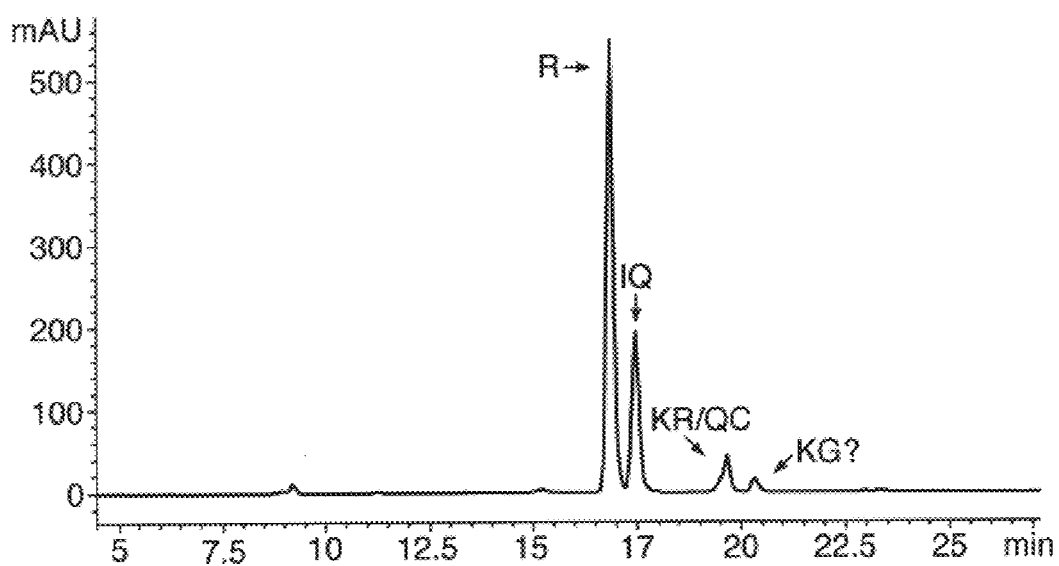
FIG. 9 shows a typical HPLC chromatogram, recorded at 360 nm, of a non-hydrolysed extract of peel tissue of a tomato plant transformed with pBBC50 (plant number C87). The major peaks correspond to rutin (R), isoquercitrin (IQ), kaempferol rutinoside/quercetin glycoside (KR/QG) (co-eluting compounds) and a putative kaempferol glycoside (KG) are marked.

Using non-hydrolysed extracts, subsequently it is analysed in which form the flavonoids accumulated in the tomato peel of pBBC50 transformed plants. FIG. 9 shows an example of HPLC chromatograms obtained with non-hydrolysed peel extracts from a pBBC50 transformed tomato. As with the control FM6203 peel, rutin (RT=16.0 min) represents the major quercetin glycoside which accumulates in the peel of the pBBC50 transformed tomato. In addition, significant amounts of isoquercitrin (quercetin 3-glucoside) (RT=17.4 min) also accumulate in the pBBC50 peel. The peak at 19.7 min appeared to contain a mixture of two compounds: the retention time and absorbance spectra of the major component corresponded to that of kaempferol rutinoside, whilst that of the minor component has an absorbance spectrum comparable to that of a quercetin glycoside. The small peak at 20.3 min has an absorbance spectrum comparable to kaempferol-3-rutinoside, but its higher RT value indicates a yet unknown kaempferol-glycoside.

Quercetin and kaempferol aglycons, all clearly present in the hydrolysed extracts, are not detectable in the non-hydrolysed peel extracts of pBBC50 transformed tomatoes. Therefore, applicants believe that these compounds are fully derived from hydrolysis of their respective glycosides. No anthocyanins accumulate in the transformed red tomatoes, as is obvious from the absence of any peak in the chromatograms recorded at 520 nm (not shown).

TABLE 1

Overview of PCR primers and adapters used.

| primer * | sequence (5' to 3') |
|---|---|
| gus2 | GCATCACGCAGTTCAACGCTG (SeQ ID 3) |
| 300 35S | CGCAAGACCCTTCCTCTATATAAG (SeQ ID 4) |
| nos ant | CCGGCAACAGGATTCAATCTT (SeQ ID 5) |
| chi 5 | GGTCGTGCCATTGAGAAGTT (SeQ ID 6) |
| nptII a | GAGGCGATTCGGCTATGACTG (SeQ ID 7) |
| npt IIb | ATCGGGAGCGGCGATACCGTA (SeQ ID 8) |
| F7 | AATTGCACCGGTCG (SeQ ID 9) |
| F8 | GATCCGACCG (SeQ ID 10) |
| F9 | TAGCCATGGG (SeQ ID 11) |
| F10 | TCGACCCATGGCTAAT (SeQ ID 12) |
| F12 | CCCGTCGACTTTCCCCGATCGTTCAAACATTTGGC (SeQ ID 13) |
| F13 | CCCGGATCCAAAAATGGTGACAGTCGAGG (SeQ ID 14) |
| F14 | CCGGTCGACGCAAATACATTCATGGCAAACG (SeQ ID 15) |
| F15 | GGCGGATCCAAAAATGTCTCCTCCAGTGTC (SeQ ID 16) |
| F16 | CCCGTCGACCTAAACTAGACTCCAATCACT (SeQ ID 17) |
| F20 | CGGGGATCCAGAGGGCCTAACTTCTGTATAGAC (SeQ ID 18) |
| F21 | CCCGTCGACTCGCGAAGATATAGCTAATCG (SeQ ID 19) |
| F38 | AATTGGGCGCGCCAAGCTTCCGAATTCTTAATTAAG (SeQ ID 20) |
| F39 | AGCTCTTAATTAAGAATTCGGAAGCTTGGCGCGCCC (SeQ ID 21) |
| AB13 | CCCATCGATGCGTCTAGTAACATAGATGAC (SeQ ID 22) |

* Adapters are made by combining two primers, heating to 95° C. for 5' and anneal both primers by cooling slowly to room temperature.

TABLE II

Flavonoid level in peel of transformed plants

| Line number | [Quercetin] μg/g dry weight peel | [Kaempferol] μg/g dry weight peel | [Naringenin] μg/g dry weight peel |
|---|---|---|---|
| G4 | 115 | 15 | 280 |
| G2 | 206 | 32 | 1095 |
| G95 | 210 | 45 | 980 |
| G3 | 253 | 27 | 523 |
| G96 | 265 | 45 | 625 |

TABLE II-continued

Flavonoid level in peel of transformed plants

| Line number | [Quercetin] μg/g dry weight peel | [Kaempferol] μg/g dry weight peel | [Naringenin] μg/g dry weight peel |
|---|---|---|---|
| G97 | 345 | 55 | 1150 |
| C69 | 115 | 10 | 105 |
| C102 | 190 | 20 | 280 |
| C41 | 208 | 28 | 789 |
| C22 | 215 | 40 | 235 |
| C54 | 230 | 40 | 410 |
| C73 | 250 | 35 | 930 |
| C6 | 300 | 15 | 375 |
| C10 | 301 | 37 | 383 |
| C64 | 320 | 35 | 470 |
| C24 | 325 | 35 | 545 |
| C53 | 350 | 65 | 345 |
| C33 | 388 | 55 | 2107 |
| C120 | 530 | 45 | 230 |
| C51 | 690 | 217 | 43 |
| C57 | 750 | 130 | 830 |
| C56 | 1490 | 100 | 270 |
| C48 | 2530 | 215 | 60 |
| C9 | 3155 | 95 | 80 |
| C34 | 3375 | 175 | 75 |
| C118 | 4355 | 615 | 65 |
| C25 | 4445 | 455 | 70 |
| C88 | 4850 | 570 | 115 |
| C86 | 4980 | 510 | 130 |
| C39 | 5540 | 325 | 80 |
| C65 | 6203 | 596 | 80 |
| C72 | 6372 | 951 | 20 |
| C49 | 6970 | 735 | 50 |
| C40 | 7244 | 1147 | 40 |
| C67 | 7405 | 900 | 80 |
| C38 | 7795 | 735 | 50 |
| C11 | 7995 | 805 | 135 |
| C103 | 8705 | 840 | 105 |
| C104 | 10055 | 870 | 110 |
| C66 | 10885 | 1370 | 70 |
| C87 | 13410 | 1250 | 95 |
| C20 | 16520 | 2048 | 80 |

Legend: HPLC analysis of flavonoid aglycons in hydrolysed peel extracts of transgenic tomatoes transformed with either PSJ89 (G series) or pBBC 50 (C series)

Sequence Listings

Sequence ID No 1

Amino acid sequence of chalcone isomerase isolated from petunia: Source: van Tunen et al, EMBO J. 7, 1257–1263, Pir database accession number S04725.

MSPPVSVTKMQVENYAFAPTVNPAGST-NTLFLAGAGHRGLEIEGKFVKFTAIGVYLEESA IPFLAEKWKGKTPQELTDSVEFFRDVVT-GPFEKFTRVTMILPLTGKQYSEKVAENCVAHW KGIG-TYTDDEGRAIEKFLDVFRSETFPP-GASIMFTQSPLGLLTISFAKDDSVTGTANAVI ENKQLSEAVLESIIGKHGVSPAAKCS-VAERVAELLKKSYAEEASVFGKPETEKSTIPVIG V

Sequence ID No 2

Nucleotide sequence encoding for protein with chalcone isomerase activity.

Source: van Tunen et al, EMBO J. 7, 1257–1263, 1988 EMBL database accession number: X14589

```
atgtctcctccagtgtccgttactaa    aatgcaggtt gagaattacg ctttcgcacc
gaccgtgaaccctgctggttccaccaatac cttgttcctt gctggtgctg ggcatagagg
tctggagatagaagggaagtttgttaagtt tacggcgata ggtgtgtatc tagaagagag
tgctattccttttctggccgaaaaatggaa aggcaaaacc cccaggagt tgactgactc
ggtcgagttctttagggatgttgttacagg tccatttgag aaatttactc gagttactat
gatcttgcccttgacgggcaagcagtactc ggagaaggtg gcggagaatt gtgttgcgca
ttggaagggataggaacgtatactgatga tgagggtcgt gccattgaga agtttctaga
tgttttccggagtgaaacttttccacctgg tgcttccatc atgtttactc aatcacccct
agggttgttgacgattagcttcgctaaaga tgattcagta actggcactg cgaatgctgt
tatagagaacaagcagttgtctgaagcagt gctggaatca ataattggga agcatggagt
ttctcctgcggcaaagtgtagtgtcgctga aagagtagcg gaactgctca aaaagagcta
tgctgaagaggcatctgtttttggaaaacc ggagaccgag aaatctacta ttccagtgat
tggagtctagttt
```

---

What is claimed is:

1. A method for producing a tomato plant which exhibits an increased level of one or more of kaempferol, quercitin, kaempferol glycosides, or quercitin glycosides in the peel tissue of its fruit, said method comprising incorporating into a tomato plant genome one or more nucleotide sequences encoding a chalcone isomerase.

2. The method according to claim 1 wherein said one or more nucleotide sequences are isolated from a species selected from the group consisting of tomato, petunia, maize, pea, Arabidopsis, bean, and grape.

3. The method according to claim 1 wherein said one or more nucleotide sequences are isolated from petunia.

4. The method according to claim 1 wherein the flavonol in said transformed plant is at least 4 times higher than in a corresponding untransformed plant.

5. The method according to claim 1, wherein said one or more nucleotide sequences each encode an amino acid sequence having at least 60% similarity to the sequence as set forth in SEQ ID NO:1.

6. The method according to claim 1 wherein said one or more nucleotide sequences each encode an amino acid sequence having at least 90% similarity to SEQ ID NO:1.

7. The method according to claim 1 wherein said one or more nucleotide sequences each comprises a sequence which has at least 50% identity to SEQ ID NO: 1.

8. The method according to claim 1 wherein said one or more nucleotide sequences encoding a chalcone isomerase are operably linked to a promoter.

9. The method according to claim 8 wherein the promoter is selected from the group consisting of:

(a) a constitutive promoter;

(b) a fruit specific promoter; and (c) a GBSS (granular bound starch synthase) promoter.

10. The method according to claim 9 wherein the promoter is a fruit specific promoter selected from the group consisting of PG, 2A11, E8, E4, and fpb11.

11. A tomato plant having one or more transgenes encoding a chalcone isomerase incorporated into its genome, wherein said plant has an increased level of one or more of kaempferol, quercitin, kaempferol glycosides, or quercitin glycosides in the peel tissue of its fruit compared to a corresponding untransformed plant.

12. Seeds or progeny plants of a tomato plant according to claim 11, wherein said seeds or progeny plants comprise said one or more transgenes encoding a chalcone isomerase incorporated into its genome.

13. Tomato fruit of a plant according to claim 11 wherein said fruit exhibit increased levels of one or more of kaempferol, quercitin, kaempferol glycosides, or quercitin glycosides in its peel tissue.

* * * * *

SEQUENCE LISTING

<160> NUMBER OF SEQ ID NOS: 23

<210> SEQ ID NO 1
<211> LENGTH: 241
<212> TYPE: PRT
<213> ORGANISM: PETUNIA HYBRIDA

<400> SEQUENCE: 1

```
Met Ser Pro Pro Val Ser Val Thr Lys Met Gln Val Glu Asn Tyr Ala
 1               5                   10                  15

Phe Ala Pro Thr Val Asn Pro Ala Gly Ser Thr Asn Thr Leu Phe Leu
                20                  25                  30

Ala Gly Ala Gly His Arg Gly Leu Glu Ile Glu Gly Lys Phe Val Lys
            35                  40                  45

Phe Thr Ala Ile Gly Val Tyr Leu Glu Glu Ser Ala Ile Pro Phe Leu
        50                  55                  60

Ala Glu Lys Trp Lys Gly Lys Thr Pro Gln Glu Leu Thr Asp Ser Val
65                  70                  75                  80

Glu Phe Phe Arg Asp Val Val Thr Gly Pro Phe Glu Lys Phe Thr Arg
                85                  90                  95

Val Thr Met Ile Leu Pro Leu Thr Gly Lys Gln Tyr Ser Glu Lys Val
            100                 105                 110

Ala Glu Asn Cys Val Ala His Trp Lys Gly Ile Gly Thr Tyr Thr Asp
        115                 120                 125

Asp Glu Gly Arg Ala Ile Glu Lys Phe Leu Asp Val Phe Arg Ser Glu
    130                 135                 140

Thr Phe Pro Pro Gly Ala Ser Ile Met Phe Thr Gln Ser Pro Leu Gly
145                 150                 155                 160

Leu Leu Thr Ile Ser Phe Ala Lys Asp Asp Ser Val Thr Gly Thr Ala
                165                 170                 175

Asn Ala Val Ile Glu Asn Lys Gln Leu Ser Glu Ala Val Leu Glu Ser
            180                 185                 190

Ile Ile Gly Lys His Gly Val Ser Pro Ala Ala Lys Cys Ser Val Ala
        195                 200                 205
```

```
Glu Arg Val Ala Glu Leu Leu Lys Lys Ser Tyr Ala Glu Glu Ala Ser
    210                 215                 220

Val Phe Gly Lys Pro Glu Thr Glu Lys Ser Thr Ile Pro Val Ile Gly
225                 230                 235                 240

Val

<210> SEQ ID NO 2
<211> LENGTH: 729
<212> TYPE: DNA
<213> ORGANISM: PETUNIA HYBRIDA

<400> SEQUENCE: 2
atgtctcctc cagtgtccgt tactaaaatg caggttgaga attacgcttt cgcaccgacc    60
gtgaaccctg ctggttccac caataccttg ttccttgctg gtgctgggca tagaggtctg   120
gagatagaag ggaagtttgt taagtttacg gcgataggtg tgtatctaga agagagtgct   180
attccttttc tggccgaaaa atggaaaggc aaaaccccccc aggagttgac tgactcggtc   240
gagttcttta gggatgttgt tacaggtcca tttgagaaat ttactcgagt tactatgatc   300
ttgcccttga cgggcaagca gtactcggag aaggtggcgg agaattgtgt tgcgcattgg   360
aaggggatag aacgtatac tgatgatgag ggtcgtgcca ttgagaagtt tctagatgtt   420
ttccggagtg aaacttttcc acctggtgct tccatcatgt ttactcaatc accctaggg   480 ttgttgacga ttagcttcgc taaagatgat tcagtaactg gcactgcgaa tgctgttata   540
gagaacaagc agttgtctga agcagtgctg gaatcaataa ttgggaagca tggagtttct   600
cctgcggcaa agtgtagtgt cgctgaaaga gtagcggaac tgctcaaaaa gagctatgct   660
gaagaggcat ctgttttggg aaaaccggag accgagaaat ctactattcc agtgattgga   720
gtctagttt                                                           729

<210> SEQ ID NO 3
<211> LENGTH: 21
<212> TYPE: DNA
<213> ORGANISM: Artificial Sequence
<220> FEATURE:
<223> OTHER INFORMATION: Description of Artificial Sequence:PRIMER

<400> SEQUENCE: 3
gcatcacgca gttcaacgct g                                               21

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence:PRIMER

<400> SEQUENCE: 4
cgcaagaccc ttcctctata taag                                            24

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:PRIMER

<400> SEQUENCE: 5
ccggcaacag gattcaatct t                                               21
```

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:PRIMER

<400> SEQUENCE: 6
ggtcgtgcca ttgagaagtt                                                    20

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence:PRIMER

<400> SEQUENCE: 7
gaggcgattc ggctatgact g                                                  21

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence:PRIMER

<400> SEQUENCE: 8
atcgggagcg gcgataccgt a                                                  21

<210> SEQ ID NO 9
<211> LENGTH: 14
<212> TYPE: DNA
<213> ORGANISM: Artificial Sequence
<220> FEATURE:
<223> OTHER INFORMATION: Description of Artificial Sequence:ADAPTER

<400> SEQUENCE: 9
aattgcaccg gtcg                                                          14

<210> SEQ ID NO 10
<211> LENGTH: 10
<212> TYPE: DNA
<213> ORGANISM: Artificial Sequence
<220> FEATURE:
<223> OTHER INFORMATION: Description of Artificial Sequence:ADAPTER

<400> SEQUENCE: 10
gatccgaccg                                                               10

<210> SEQ ID NO 11
<211> LENGTH: 10
<212> TYPE: DNA
<213> ORGANISM: Artificial Sequence
<220> FEATURE:
<223> OTHER INFORMATION: Description of Artificial Sequence:ADAPTER

<400> SEQUENCE: 11
tagccatggg                                                               10

<210> SEQ ID NO 12
<211> LENGTH: 16
<212> TYPE: DNA
<213> ORGANISM: Artificial Sequence
<220> FEATURE:
<223> OTHER INFORMATION: Description of Artificial Sequence:ADAPTER

<400> SEQUENCE: 12
tcgacccatg gctaat                                                    16

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence:PRIMER

<400> SEQUENCE: 13
cccgtcgact ttccccgatc gttcaaacat ttggc                               35

<210> SEQ ID NO 14
<211> LENGTH: 29
<212> TYPE: DNA
<213> ORGANISM: Artificial Sequence
<220> FEATURE:
<223> OTHER INFORMATION: Description of Artificial Sequence:PRIMER

<400> SEQUENCE: 14
cccggatcca aaaatggtga cagtcgagg                                      29

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence:PRIMER

<400> SEQUENCE: 15
ccggtcgacg caaatacatt catggcaaac g                                   31

<210> SEQ ID NO 16
<211> LENGTH: 30
<212> TYPE: DNA
<213> ORGANISM: Artificial Sequence
<220> FEATURE:
<223> OTHER INFORMATION: Description of Artificial Sequence:PRIMER

<400> SEQUENCE: 16
ggcggatcca aaaatgtctc ctccagtgtc                                     30

<210> SEQ ID NO 17
<211> LENGTH: 30
<212> TYPE: DNA
<213> ORGANISM: Artificial Sequence
<220> FEATURE:
<223> OTHER INFORMATION: Description of Artificial Sequence:PRIMER

<400> SEQUENCE: 17
cccgtcgacc taaactagac tccaatcact                                     30

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence:PRIMER

<400> SEQUENCE: 18
cggggatcca gagggcctaa cttctgtata gac                                 33

<210> SEQ ID NO 19

```
<211> LENGTH: 30
<212> TYPE: DNA
<213> ORGANISM: Artificial Sequence
<220> FEATURE:
<223> OTHER INFORMATION: Description of Artificial Sequence:PRIMER

<400> SEQUENCE: 19
cccgtcgact cgcgaagata tagctaatcg                                       30

<210> SEQ ID NO 20
<211> LENGTH: 36
<212> TYPE: DNA
<213> ORGANISM: Artificial Sequence
<220> FEATURE:
<223> OTHER INFORMATION: Description of Artificial Sequence:ADAPTER

<400> SEQUENCE: 20
aattgggcgc gccaagcttc cgaattctta attaag                                36

<210> SEQ ID NO 21
<211> LENGTH: 36
<212> TYPE: DNA
<213> ORGANISM: Artificial Sequence
<220> FEATURE:
<223> OTHER INFORMATION: Description of Artificial Sequence:ADAPTER

<400> SEQUENCE: 21
agctcttaat taagaattcg gaagcttggc gcgccc                                36

<210> SEQ ID NO 22
<211> LENGTH: 30
<212> TYPE: DNA
<213> ORGANISM: Artificial Sequence
<220> FEATURE:
<223> OTHER INFORMATION: Description of Artificial Sequence:PRIMER

<400> SEQUENCE: 22
cccatcgatg cgtctagtaa catagatgac                                       30

<210> SEQ ID NO 23
<211> LENGTH: 91
<212> TYPE: DNA
<213> ORGANISM: Artificial Sequence
<220> FEATURE:
<223> OTHER INFORMATION: Description of Artificial Sequence:MULTIPLE
      CLONING SITE

<400> SEQUENCE: 23
ggcgcgccaa gcttgcatgc atcgatatgg tcgactctag aggatccccg ggtaccgagc      60
tcgaattcca gatctgcggc cgcttaatta a                                     91
```